United States Patent
Ray et al.

(10) Patent No.: US 11,567,084 B2
(45) Date of Patent: Jan. 31, 2023

(54) MICROWAVE ENHANCED ENZYMATIC REACTOR FOR PROTEOMICS BY MASS SPECTROMETRY

(71) Applicant: Research Foundation for State University of New York, Buffalo, NY (US)

(72) Inventors: Steven J. Ray, Williamsville, NY (US); Maria Elisa Rivera-Albarran, Amherst, NY (US)

(73) Assignee: The Research Foundation for the State University of New York, Amherst, NY (US)

( * ) Notice: Subject to any disclaimer, the term of this patent is extended or adjusted under 35 U.S.C. 154(b) by 274 days.

(21) Appl. No.: 16/871,678

(22) Filed: May 11, 2020

(65) Prior Publication Data

US 2020/0378985 A1    Dec. 3, 2020

Related U.S. Application Data

(60) Provisional application No. 62/846,274, filed on May 10, 2019.

(51) Int. Cl.
| | |
|---|---|
| *G01N 33/68* | (2006.01) |
| *C12Q 1/37* | (2006.01) |
| *G01N 1/44* | (2006.01) |
| *B01J 19/12* | (2006.01) |
| *G01N 30/72* | (2006.01) |
| *H01J 49/36* | (2006.01) |
| *H01J 49/16* | (2006.01) |
| *G01N 30/02* | (2006.01) |

(52) U.S. Cl.
CPC ........ *G01N 33/6848* (2013.01); *B01J 19/126* (2013.01); *C12Q 1/37* (2013.01); *G01N 1/44* (2013.01); *G01N 30/7266* (2013.01); *H01J 49/165* (2013.01); *H01J 49/36* (2013.01); *B01J 2219/1206* (2013.01); *G01N 2030/027* (2013.01); *G01N 2570/00* (2013.01)

(58) Field of Classification Search
None
See application file for complete search history.

(56) References Cited

PUBLICATIONS

Chen, Z. et al. Development of continuous microwave-assisted protein digestion with immobilized enzyme, Biochemical and Biophysical Research Communications, 445 (2014) 491-496 (Year: 2014).*

(Continued)

*Primary Examiner* — Xiaoyun R Xu
(74) *Attorney, Agent, or Firm* — Woods Oviatt Gilman LLP; Katherine H. McGuire, Esq.

(57) ABSTRACT

A microwave microstrip resonator apparatus including a housing; a resonator within the housing; an output conductor within the housing and spaced apart from the resonator so as to define a capacitive gap therebetween; a reaction vessel configured to reside with the capacitive gap; and a power supply coupled to the resonator whereby contents within the reaction vessel are heated when energy is supplied to the resonator by the power supply. A mass spectrometer may also be coupled to an outlet end of the reaction vessel such that the contents within the reaction vessel are, simultaneously, delivered to the mass spectrometer for analysis.

20 Claims, 31 Drawing Sheets
(18 of 31 Drawing Sheet(s) Filed in Color)

(56) References Cited

PUBLICATIONS

Villegas, L. On-line protein digestion by immobilized enzyme microreactor capillary electrophoresis-mass spectrometry, Talanta 199 (2019) 116-123 (Year: 2019).*

Villegas, L. On-line protein digestion by immobilized enzyme microreactor capillary electrophoresis-mass spectrometry, Talanta 199 (2019) 116-123 (Year: 2019) Supplemental information.*

* cited by examiner

| Peptide Sequence of Myoglobin | Theoretical (m/z) | Experimental 10-h Conventional (m/z) | Experimental 20 W-10 min (m/z) | Missed Cleavage |
|---|---|---|---|---|
| $T_{1-17}$ GLSDGEWQQVLNVWGK | 1815.9 (Met Loss) | 908.6 (2+) | 1815.6 (1+) 908.8 (2+) | 0 |
| $T_{18-32}$ VEADIAGHGQEVLIR | 1606.9 | 804.1 (2+) | 803.8 (2+) | 0 |
| $T_{1-32}$ MGLSDGEWQQVL...EVLIR | 3403.7 (Met Loss) | - | 1702.8 (2+) 1135.8 (3+) 852.1 (4+) | 1 |
| $T_{33-43}$ LFTGHPETLEK | 1271.7 | 1271.8 (1+) 636.5 (2+) | - | 0 |
| $T_{44-48}$ FDKFK | 684.4 | 684.4 | 684.3 | 1 |
| $T_{49-57}$ HLKTEAEMK | 1086.6 | - | 1086.6 | 1 |
| $T_{52-57}$ TEAEMK | 708.4 | 708.4 | - | 0 |
| $T_{58-64}$ ASEDLKK | 790.4 | - | 790.3 | 1 |
| $T_{58-63}$ ASEDLK | 662.4 | 662.4 | - | 0 |
| $T_{65-78}$ HGTWLTALGGILK | 1378.8 | 1378.7 (1+) 689.8 (2+) | 1378.8 (1+) 689.9 (2+) | 0 |
| $T_{81-97}$ GHHEAELKPLAQSHATK | 1854.0 | 927.1 (2+) | - | 1 |
| $T_{81-99}$ GHHEAELKPLAQSHATKHK | 2119.1 | - | 1061.7 (2+) | 1 |
| $T_{104-119}$ YLEFISDAIHVLHSK | 1885.0 | 1885.8 (1+) 943.7 (2+) | 1885.0 (1+) 943.5 (2+) | 0 |
| $T_{120-134}$ HPGDFGADAQGAMTK | 1502.7 | - | 1502.6 (1+) 751.8 (2+) | 0 |
| $T_{135-140}$ ALELFR | 748.4 | 748.6 | 748.5 | 0 |
| $T_{141-146}$ NDIAAK | 631.3 | 631.4 | 631.3 | 0 |
| $T_{149-154}$ ELGFQG | 650.3 | 650.4 | 650.3 | 0 |

FIG. 7

| Peptide Sequence of Cytochrome c | Theoretical (m/z) | Experimental 20-h Conventional (m/z) | Experimental 20 W-2 min (m/z) | Experimental 20 W-5 min (m/z) | Experimental 20 W-10 min (m/z) | Missed Cleavage |
|---|---|---|---|---|---|---|
| $T_{1-6}$ MGDVEK | 589.3 (Met loss+Acetyl) | 589.2 | 589.4 | 589.4 | 589.2 | 0 |
| $T_{10-14}$ IFVQK | 634.4 | 634.3 | - | - | 634.3 | 0 |
| $T_{10-23}$ IFVQKCAQCHTVEK | 1633.8 | 1633.4 | - | - | 817.1(2+) | 1 |
| $T_{27-39}$ HKTGPNLHGLFGR | 1433.8 | 717.7(2+) | - | 718.0 (2+) | 717.8 (2+) | 1 |
| $T_{29-39}$ TGPNLHGLFGR | 1168.6 | 1168.5 | - | 1168.7 | 1168.5 | 0 |
| $T_{29-40}$ TGPNLHGLFGRK | 1296.7 | 1296.6 | - | 1296.8 | 1296.6 | 1 |
| $T_{41-54}$ TGQAPGFSYTDANK | 1456.7 | 1456.5 | - | - | 1456.5 | 0 |
| $T_{41-56}$ TGQAPGFSYTDANKNK | 1698.8 | - | - | 850.7 (2+) | 849.7 (2+) | 1 |
| $T_{55-73}$ NKGITWGEETLMEYLENPK | 2252.1 | 1125.3 (2+) | - | - | 1125.3 (2+) | 1 |
| $T_{57-73}$ GITWGEETLMEYLENPK | 2009.9 | 1005.7 (2+) | - | - | 1005.7 (2+) | 0 |
| $T_{57-74}$ GITWGEETLMEYLENPKK | 2138.0 | 1069.8 (2+) | - | - | 1069.8 (2+) | 1 |
| $T_{75-80}$ YIPGTK | 678.4 | 678.3 | 678.4 | 678.4 | 678.3 | 0 |
| $T_{81-87}$ MIFAGIK | 779.4 | 779.4 | 779.6 | 779.5 | 779.4 | 0 |
| $T_{81-88}$ MIFAGIKK | 907.5 | 907.5 | - | 907.6 | 907.4 | 1 |
| $T_{89-92}$ KGER | 489.3 | 489.1 | - | - | 489.1 | 1 |
| $T_{93-100}$ EDLIAYLK | 964.5 | 964.4 | - | - | - | 0 |
| $T_{101-105}$ KATNE | 562.2 | 562.3 | - | 562.3 | 562.1 | 1 |
| $T_{102-105}$ ATNE | 434.2 | 434.2 | - | - | - | 0 |

FIG. 9

| Peptide Sequence of β-casein | Theoretical (m/z) | Experimental 10-h Conventional (m/z) | Experimental 20 W-2 min (m/z) | Experimental 20 W-5 min (m/z) | Experimental 20 W-10 min (m/z) | Missed Cleavage |
|---|---|---|---|---|---|---|
| $T_{41-43}$ INK | 374.4 | 374.1 | - | 374.4 | 374.4 | 0 |
| $T_{41-44}$ INKK | 502.3 | - | - | - | 502.6 | 1 |
| $T_{44-47}$ KIEK | 517.3 | 517.3 | - | 517.5 | 517.5 | 1 |
| $T_{113-120}$ VKEAMAPK | 873.5 | 873.5 | 873.5 | 873.7 | 873.8 | 1 |
| $T_{115-120}$ EAMAPK | 646.3 | 646.3 | 646.3 | 646.5 | 646.6 | 0 |
| $T_{121-128}$ VKEMPFPK | 1013.5 | 1013.5 | - | 1013.8 | 1013.8 | 1 |
| $T_{123-128}$ EMPFPK | 748.4 | - | - | 748.5 | 748.6 | 0 |
| $T_{129-184}$ YPVEPFTESQSLTLTDVENLHLPLPLLQSWMHQPHQPLPPTVMFPPQSVLSLSQSK | 6359.3 | 1591.5 (4+) 1273.4 (5+) | - | - | 1591.8 (4+) 1273.6 (5+) | 0 |
| $T_{185-191}$ VLPVPQK | 780.5 | 780.5 | 780.5 | 780.7 | 780.8 | 0 |
| $T_{192-198}$ AVPYPQR | 830.5 | 830.5 | 830.4 | 830.7 | 830.8 | 0 |
| $T_{199-217}$ DMPIQAFLLYQEPVLGPVR | 2186.2 | 1093.9 (2+) | - | - | - | 0 |
| $T_{199-224}$ DMPIQAFLLYQEPVLGPVR | 2910.6 | 1455.7 (2+) | - | 1456.2 (2+) | 1456.0 (2+) | 0 |
| $T_{218-224}$ GPFPIIV | 742.4 | 742.4 | - | 742.3 | 742.4 | 0 |

FIG. 11

| Peptide Sequence of Ubiquitin | Theoretical (m/z) | Experimental 20 W-5 min (m/z) | Experimental 20 W-10 min (m/z) | Experimental 20 W-15 min (m/z) | Missed Cleavage |
|---|---|---|---|---|---|
| $T_{1-6}$ MQIFVK | 765.4 | 765.4 | 765.4 | 765.4 | 0 |
| $T_{7-11}$ TLTGK | 519.3 | 519.2 | 519.2 | 519.1 | 0 |
| $T_{12-27}$ TITLEVEPSDTIENVK | 1787.9 | 894.4 (2+) | 894.8 (2+) | 894.8 (2+) | 0 |
| $T_{12-29}$ TITLEVEPSDTIENVKAK | 1987.1 | 994.4 (2+) | 994.4 (2+) | 994.4 (2+) | 1 |
| $T_{34-42}$ EGIPPDQQR | 1039.5 | - | - | 1039.8 (1+) 520.0 (2+) | 0 |
| $T_{43-48}$ LIFAGK | 648.4 | 648.4 | 648.4 | 648.4 | 0 |
| $T_{43-54}$ LIFAGKQLEDGR | 1346.7 | - | - | 673.8 (2+) | 1 |
| $T_{49-54}$ QLEDGR | 717.4 | - | 717.4 | 717.6 | 0 |
| $T_{55-63}$ TLSDYNIQK | 1081.5 | - | 541.1 (2+) | 541.5 (2+) | 0 |
| $T_{55-72}$ TLSDYNIQKESTLHLVLR | 2130.2 | 1066.0 (2+) 710.5 (3+) | 1065.9 (2+) 710.5 (3+) | 1066.0 (2+) 710.5 (3+) | 1 |
| $T_{73-76}$ LRGG | 402.2 | 402.3 | 402.3 | 402.4 | 1 |

FIG. 14

| Peptide Sequence of Cytochrome c using Lys-C | Theoretical (m/z) | Experimental 20-h Conventional (m/z) | Experimental 20 W-2 min (m/z) | Experimental 20 W-5 min (m/z) | Experimental 20 W-10 min (m/z) | Missed Cleavage |
|---|---|---|---|---|---|---|
| $T_{1-6}$ MGDVEK | 589.3 (Met loss+Acetyl) | - | - | 588.8 | 588.9 | 0 |
| $T_{7-9}$ GKK | 332.2 | 331.8 | 331.8 | 331.7 | 331.8 | 1 |
| $T_{10-14}$ IFVQK | 634.4 | 634.1 | - | 633.8 | 634.0 | 0 |
| $T_{10-23}$ IFVQKCAQ...VEK | 1633.8 | 1633.5 | - | 1633.3 | 1633.4 | 1 |
| $T_{24-26}$ GGK | 261.2 | 260.7 | - | 260.6 | 260.6 | 0 |
| $T_{27-28}$ HK | 284.2 | 283.8 | - | 283.6 | 283.7 | 0 |
| $T_{27-40}$ HKTGPNLHGLFGRK | 1561.9 | - | - | 1562.7 | 1562.8 | 1 |
| $T_{29-40}$ TGPNLHGLFGRK | 1296.7 | 1296.6 | - | 1296.5 | 1296.6 | 0 |
| $T_{41-54}$ TGQAPGFS...ANK | 1456.7 | 1456.4 | - | 1456.4 | 1456.4 | 0 |
| $T_{55-73}$ NKGITWGEE...NPK | 2252.1 | - | - | 1125.3 (2+) | 1125.3 (2+) | 1 |
| $T_{57-73}$ GITWGEETL...NPK | 2009.9 | 1005.6 (2+) | - | - | - | 0 |
| $T_{74-80}$ KYIPGTK | 806.5 | 806.2 | 806.3 | 806.1 | 806.2 | 1 |
| $T_{75-80}$ YIPGTK | 678.4 | 678.1 | 678.0 | 677.9 | 678.1 | 0 |
| $T_{81-87}$ MIFAGIK | 779.4 | 779.2 | 779.2 | 779.1 | 779.2 | 0 |
| $T_{81-88}$ MIFAGIKK | 907.5 | 907.3 | 907.3 | 907.2 | 907.3 | 1 |
| $T_{89-100}$ KGEREDLIAYLK | 1434.8 | 1434.6 | - | 1434.5 | 1434.5 | 1 |
| $T_{101-105}$ KATNE | 562.2 | 561.9 | 562.0 | 561.8 | 561.9 | 1 |

FIG. 22

| Peptide Sequence of Cytochrome c using Trypsin | Theoretical (m/z) | Experimental 20-h Conventional (m/z) | Experimental 20 W-2 min (m/z) | Experimental 20 W-5 min (m/z) | Experimental 20 W-10 min (m/z) | Missed Cleavage |
|---|---|---|---|---|---|---|
| $T_{1-6}$ MGDVEK | 589.3 (Met loss+Acetyl) | 589.2 | 589.4 | 589.4 | 589.2 | 0 |
| $T_{10-14}$ IFVQK | 634.4 | 634.3 | - | - | 634.3 | 0 |
| $T_{10-23}$ IFVQKCAQCHTVEK | 1633.8 | 1633.4 | - | - | 817.1(2+) | 1 |
| $T_{27-39}$ HKTGPNLHGLFGR | 1433.8 | 717.7(2+) | - | 718.0 (2+) | 717.8 (2+) | 1 |
| $T_{29-39}$ TGPNLHGLFGR | 1168.6 | 1168.5 | - | 1168.7 | 1168.5 | 0 |
| $T_{29-40}$ TGPNLHGLFGRK | 1296.7 | 1296.6 | - | 1296.8 | 1296.6 | 1 |
| $T_{41-54}$ TGQAPGFSYTDANK | 1456.7 | 1456.5 | - | - | 1456.5 | 0 |
| $T_{41-56}$ TGQAPGFSYTDANKNK | 1698.8 | - | - | 850.7 (2+) | 849.7 (2+) | 1 |
| $T_{55-73}$ NKGITWGEETLMEYLENPK | 2252.1 | 1125.3 (2+) | - | - | 1125.3 (2+) | 1 |
| $T_{57-73}$ GITWGEETLMEYLENPK | 2009.9 | 1005.7 (2+) | - | - | 1005.7 (2+) | 0 |
| $T_{57-74}$ GITWGEETLMEYLENPKK | 2138.0 | 1069.8 (2+) | - | - | 1069.8 (2+) | 1 |
| $T_{75-80}$ YIPGTK | 678.4 | 678.3 | 678.4 | 678.4 | 678.3 | 0 |
| $T_{81-87}$ MIFAGIK | 779.4 | 779.4 | 779.6 | 779.5 | 779.4 | 0 |
| $T_{81-88}$ MIFAGIKK | 907.5 | 907.5 | - | 907.6 | 907.4 | 1 |
| $T_{89-92}$ KGER | 489.3 | 489.1 | - | - | 489.1 | 1 |
| $T_{93-100}$ EDLIAYLK | 964.5 | 964.4 | - | - | - | 0 |
| $T_{101-105}$ KATNE | 562.2 | 562.3 | - | 562.3 | 562.1 | 1 |
| $T_{102-105}$ ATNE | 434.2 | 434.2 | - | - | - | 0 |

FIG. 23

| Peptide Sequence of Cytochrome c using Trypsin + Lys-C | Theoretical (m/z) | Experimental 20-h Conventional (m/z) | Experimental 20 W-5 min (m/z) | Experimental 20 W-10 min (m/z) | Missed Cleavage |
|---|---|---|---|---|---|
| $T_{1-6}$ MGDVEK | 589.3 (Met loss+Acetyl) | 588.9 | 588.8 | 588.8 | 0 |
| $T_{7-9}$ GKK | 332.2 | 331.8 | - | 331.7 | 1 |
| $T_{10-14}$ IFVQK | 634.4 | 634.0 | - | 633.9 | 0 |
| $T_{15-23}$ CAQCHTVEK | 1018.4 | 1016.7 | - | 1016.7 | 0 |
| $T_{10-23}$ IFVQKCAQCHTVEK | 1633.8 | - | 1633.4 | 1633.4 | 1 |
| $T_{29-39}$ TGPNLHGLFGR | 1168.6 | 1168.3 | 1168.3 | 1168.3 | 0 |
| $T_{29-40}$ TGPNLHGLFGRK | 1296.7 | 1296.5 (1+) 648.6 (2+) | 1296.4 (1+) 648.6 (2+) | 1296.5 (1+) 648.5 (2+) | 1 |
| $T_{40-54}$ KTGQAPGFSYTDANK | 1584.8 | 1584.6 | 1584.6 | 1584.7 | 1 |
| $T_{41-54}$ TGQAPGFSYTDANK | 1456.7 | 1456.5 | 1456.4 | 1456.5 | 0 |
| $T_{55-73}$ NKGITQGEETLMEYLENPK | 2252.1 | 1125.3 (2+) 561.9 (3+) | 1125.2 (2+) 561.9 (3+) | 1125.3 (2+) 561.8 (3+) | 1 |
| $T_{57-73}$ GITWGEETLMEYLENPK | 2009.9 | 1005.7 (2+) | - | - | 0 |
| $T_{74-80}$ KYIPGTK | 806.5 | 806.2 | 806.1 | 806.1 | 1 |
| $T_{75-80}$ YIPGTK | 678.4 | 678.3 | - | 678.0 | 0 |
| $T_{81-87}$ MIFAGIK | 779.4 | 779.1 | 779.1 | 779.1 | 0 |
| $T_{81-88}$ MIFAGIKK | 907.5 | 907.3 | 907.2 | 907.2 | 1 |
| $T_{89-100}$ KGEREDLIAYLK | 1434.8 | 1434.6 | 1434.5 | 1434.5 | 1 |
| $T_{101-105}$ KATNE | 562.2 | 561.9 | 561.9 | 561.8 | 1 |
| $T_{102-105}$ ATNE | 434.2 | 434.2 | - | - | 0 |

FIG. 24

| Peptide Sequence of Apomyoglobin using Lys-C | Theoretical (m/z) | Experimental 20-h Conventional (m/z) | Experimental 20 W-10 min (m/z) | Missed Cleavage |
|---|---|---|---|---|
| T$_{1-16}$ GLSDGEWQQVLNVWGK | 1815.9 | 1816.9 | - | 0 |
| T$_{1-42}$ GLSDGEWQQVLNVWGKVEADIAGHGQEVLIRLFTGHPETLEK | 2860.6 | - | 1553.4 (3+) 1165.4 (2+) | 1 |
| T$_{17-42}$ VEADIAGHGQEVLIRLFTGHPETLEK | 2860.6 | 1430.8 (2+) 954.2 (3+) | - | 0 |
| T$_{43-45}$ FDK | 409.2 | 408.9 | 408.8 | 0 |
| T$_{46-50}$ FKHLK | 672.4 | 672.0 | 672.0 | 1 |
| T$_{48-56}$ HLKTEAMK | 1086.6 | - | 1086.3 | 1 |
| T$_{51-56}$ TEAEMK | 708.3 | 708.0 | 708.0 | 0 |
| T$_{57-63}$ ASEDLKK | 790.4 | - | 790.1 | 1 |
| T$_{64-77}$ HGTVVLTALGGILK | 1378.8 | 1378.8 (1+) 689.9 (2+) | 1378.7 (1+) | 0 |
| T$_{64-78}$ HGTVVLTALGGILKK | 1506.9 | 1506.8 | 1506.8 | 1 |
| T$_{79-96}$ KGHHEAELKPLAQSHATK | 1982.1 | - | 991.8 (2+) | 1 |
| T$_{79-98}$ KGHHEAELKPLAQSHATKHK | 2248.2 | - | 1124.1 (2+) | 2 |
| T$_{80-96}$ GHHEAELKPLAQSHATK | 1854.0 | 1854.9 (1+) 927.4 (2+) | - | 0 |
| T$_{97-102}$ HKIPIK | 735.5 | 735.2 | 735.2 | 1 |
| T$_{99-102}$ IPIK | 470.3 | 470.0 | 469.9 | 0 |
| T$_{99-118}$ IPIKYLEFISDAIIHVLHSK | 2336.3 | - | 1168.7 (2+) 779.2 (3+) | 1 |
| T$_{103-118}$ YLEFISDAIIHVLHSK | 1885.0 | 1885.0 (1+) 943.3 (2+) | - | 0 |
| T$_{119-133}$ HPGDFGADAQGAMTK | 1502.7 | 1502.6 (1+) 751.7 (2+) | 1502.6 (1+) 751.6 (2+) | 0 |
| T$_{134-145}$ ALELFRNDIAAK | 1360.8 | 1360.7 (1+) 680.8 (2+) | 1360.7 (1+) | 1 |
| T$_{148-153}$ ELGFQG | 650.3 | 649.9 | 650.1 | 0 |

FIG. 25

| Peptide Sequence of Apomyoglobin using Trypsin | Theoretical (m/z) | Experimental 20-h Conventional (m/z) | Experimental 20 W-10 min (m/z) | Missed Cleavage |
|---|---|---|---|---|
| $T_{1-16}$ GLSDGEWQQVLNVWGK | 1815.9 | 1815.8 | - | 0 |
| $T_{1-31}$ GLSDGEWQQVLNVWGKVEADIAGHGQEVLIR | 3403.7 | - | 1702.8 (2+) 1135.4 (3+) | 1 |
| $T_{17-31}$ VEADIAGHGQEVLIR | 1606.9 | 1606.8 (1+) 803.7 (2+) | 1606.7 (1+) 803.9 (2+) | 0 |
| $T_{32-42}$ LFTGHPETLEK | 1271.7 | 1271.4 | 1271.4 | 0 |
| $T_{43-45}$ FDK | 409.2 | 408.7 | 408.7 | 0 |
| $T_{46-50}$ FKHLK | 672.4 | 672.0 | 671.9 | 1 |
| $T_{48-56}$ HLKTEAMK | 1086.6 | 1086.3 (1+) 543.4 (2+) | 1086.3 (1+) | 1 |
| $T_{51-56}$ TEAEMK | 708.3 | 708.0 | 708.0 | 0 |
| $T_{57-63}$ ASEDLKK | 790.4 | - | 790.1 | 1 |
| $T_{64-77}$ HGTVVLTALGGILK | 1378.8 | 1378.7 (1+) 689.7 (2+) | 1378.7 (1+) | 0 |
| $T_{80-96}$ GHHEAELKPLAQSHATK | 1854.0 | 927.3 (2+) | 1853.9 (1+) 927.3 (2+) | 0 |
| $T_{97-102}$ HKIPIK | 735.5 | 735.3 | 735.2 | 1 |
| $T_{99-102}$ IPIK | 470.3 | 470.0 | - | 0 |
| $T_{103-118}$ YLEFISDAIIHVLHSK | 1885.0 | 1886.0 (1+) 943.3 (2+) | 1885.9 (1+) 943.2 (2+) | 0 |
| $T_{119-133}$ HPGDFGADAQGAMTK | 1502.7 | 1502.5 | 1503.5 | 0 |
| $T_{134-139}$ ALELFR | 748.4 | 748.2 | 748.1 | 0 |
| $T_{134-145}$ ALELFRNDIAAK | 1360.8 | - | 1360.6 (1+) | 1 |
| $T_{140-145}$ NDIAAK | 631.3 | 630.9 | 631.0 | 1 |
| $T_{146-153}$ YKELGFQG | 941.5 | - | 941.2 | 1 |

FIG. 26

| Peptide Sequence of Apomyoglobin using Trypsin + Lys-C | Theoretical (m/z) | Experimental 20-h Conventional (m/z) | Experimental 20 W-10 min (m/z) | Missed Cleavage |
|---|---|---|---|---|
| $T_{1-16}$ GLSDGEWQQVLNVWGK | 1815.9 | 1815.8 | 1816.8 | 0 |
| $T_{1-31}$ GLSDGEWQQVLNVWGKVEADIAGHGQEVLIR | 3403.7 | - | 1702.8 (2+) 1135.2 (3+) | 1 |
| $T_{17-31}$ VEADIAGHGQEVLIR | 1606.9 | 1606.7 (1+) 803.5 (2+) | 1606.8 (1+) 803.6 (2+) | 0 |
| $T_{32-42}$ LFTGHPETLEK | 1271.7 | 1271.3 | 1271.4 | 0 |
| $T_{43-45}$ FDK | 409.2 | 408.7 | 408.7 | 0 |
| $T_{46-50}$ FKHLK | 672.4 | 671.8 | 671.9 | 1 |
| $T_{51-56}$ TEAEMK | 708.3 | 707.9 | 707.9 | 0 |
| $T_{57-63}$ ASEDLKK | 790.4 | - | 790.1 | 1 |
| $T_{64-77}$ HGTVVLTALGGILK | 1378.8 | 1378.6 (1+) 689.5 (2+) | 1378.7 (1+) 689.6 (2+) | 0 |
| $T_{80-96}$ GHHEAELKPLAQSHATK | 1854.0 | 927.1 (2+) | 1854.8 (1+) 927.2 (2+) | 0 |
| $T_{97-102}$ HKIPIK | 735.5 | 735.1 | 735.1 | 1 |
| $T_{99-102}$ IPIK | 470.3 | 469.8 | 469.8 | 0 |
| $T_{103-118}$ YLEFISDAIIHVLHSK | 1885.0 | 1885.8 (1+) 943.2 (2+) | 1886.0 (1+) 943.2 (2+) | 0 |
| $T_{119-133}$ HPGDFGADAQGAMTK | 1502.7 | 1502.4 | 1502.5 | 0 |
| $T_{134-139}$ ALELFR | 748.4 | 748.0 | 748.1 | 0 |
| $T_{140-145}$ NDIAAK | 631.3 | 630.9 | 630.9 | 1 |
| $T_{134-145}$ ALELFRNDIAAK | 1360.8 | - | 1360.6 | 1 |
| $T_{148-153}$ ELGFQG | 650.3 | 649.8 | 649.8 | 0 |

FIG. 27

MICROWAVE ENHANCED ENZYMATIC REACTOR FOR PROTEOMICS BY MASS SPECTROMETRY

CROSS REFERENCE TO RELATED APPLICATIONS

This application claims the benefit of U.S. Provisional Patent Application No. 62/846,274, filed May 10, 2019, entitled MICROWAVE ENHANCED ENZYMATIC REACTOR FOR PROTEOMICS BY MASS SPECTROMETRY, the entirety of which is incorporated herein by reference.

GOVERNMENT SUPPORT

This invention was made with government support under Grant No. CHE-1622531, awarded by the National Science Foundation.

The government has certain rights in the invention.

FIELD OF THE INVENTION

The present invention generally relates to proteomics, and more particularly to a system and method for characterizing proteins via mass spectrometry, and still more particularly to a microwave enhanced enzymatic reactor for conducting proteomics via mass spectrometry.

BACKGROUND OF THE INVENTION

Enzymatic protein digestion is a crucial tool for protein characterization by mass spectrometry (MS) using what is termed as a "bottom-up" analysis approach. Essentially, proteins are digested using either chemical or enzymatic agents to form a series of peptide fragments which can then be analyzed by MS, with the primary protein sequence then inferred from the fragment information. Although this process is able to provide enough information for protein identification through peptide sequencing it does suffer from some drawbacks; with the most problematic being the requirement of long incubation times (e.g. days) and the need for sample treatment prior to and after the digestion step.

Microwave heating systems can be used as a method to accelerate the rates of chemical reactions, thereby reducing digestion times (often from hours to a couple minutes), while also providing a yield of protein fragment coverage similar to those obtained with long-time incubation digestions. Microwave acceleration of chemical reactions is a common practice, and several vendors offer scientific microwave digestion systems. However, current used microwave systems for this purpose do not necessarily take full advantages of the field focusing capabilities of microwave radiation. Scientific microwave ovens (e.g. CEM, Anton Parr, etc.) are by far the most commonly used systems to carry out chemical reactions, requiring constant movement of the sample after being irradiated. Microwave ovens operating at 2.45 GHz are the preferred approach to carry out microwave heating due to their wide availability and low cost. More advanced single-mode microwave systems are also common; however, these are used in much larger reaction volumes. Such ovens produce uneven heating due to irregular distribution of microwave energy inside the cavity and are thus unsuitable for routine use in MS.

SUMMARY OF THE INVENTION

Because enzymatic digestion methods are routinely used for mass spectrometry (MS) bottom-up analysis, a comprehensive reaction system designed expressly for MS analysis that is also able to incorporate microwave heating is desirable to provide significant benefits. A specialized microstrip microwave half-wave (HW) resonator has been shown to provide enhanced field focusing at specific and localized regions allowing efficient and very specific volumetric heating of small volumes, and in accordance with an aspect of the present invention, this specialized miniaturized resonator along with micro-volume reaction cells are utilized to digest complex protein systems rapidly and efficiently, often leading to reductions of digestion times from days to mere minutes. Moreover, the geometry of the system permits the system to be directly incorporated into MS sample introduction systems, thereby permitting samples to be digested and then analyzed in a single step (e.g. with little or no sample manipulation). The system may also be used with in-line chromatographic separation systems to permit on-line digestion of proteins separated by chromatography.

As will be described more fully in the following, a HW microstrip resonator system in accordance with the present invention may greatly increase rates of reaction, and thus reduce digestion times, thereby yielding comparable protein sequence coverages to those obtained from conventional digestion processes. The designed HW microstrip resonator can be implemented as a microwave reactor allowing sample to be irradiated with microwaves inside a microcapillary while it is being characterize with, for example, a mass spectrometer.

Since the confinement of the microwave field is crucial for microreaction volumes, a microwave waveguide is a unique solution for localized, high-intensity heating and consequently is much faster and simpler than existing approaches. The waveguide is able to focus the electric field into a finite region which allows localized heating within the sample being used. The design is energy efficient in the sense that small amounts of power are required to provide sufficient localized field. The designed HW microstrip resonator provides the advantage of simple and fast manufacture, and very low cost since solid-state amplifiers of low power can be used off-the-shelf. In addition, the designed system may further combine the capabilities of a microwave resonator and a nano-electrospray ionization (nanoESI or nanospray) emitter, allowing both reaction vessel (microreactor) and mass spectrometry characterization in the same device.

In addition, because a nanoESI emitter is used as the reaction vessel and MS ionization source, sample requirements and overall treatment are greatly reduced. This represents a more efficient way to process samples where the available amount of material is limited. Moreover, in accordance with the present invention, the following systems may also carry out microwave-assisted enzymatic digestions online while recording mass spectra, simultaneously, without the requirement of further sample treatments or handling. Alternatively, the process may be carried out independently due to the incorporation of external power supplies. As a result, organic and inorganic synthesis can take advantage of the reduced reaction times and sample handling while the proteomic field can also use this technology for faster protein digestion times with comparable sequence coverages, but without the requirement of large sample volumes.

In a further aspect of the present invention, the reaction vessel (microcapillary) can be substituted with different materials with different interaction (dielectric) within microwave fields. For instance, coated capillaries can be used to allow proteins to be digested by immobilized enzymatic systems while exposed to microwave field.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 is a table of the tryptic peptides with m/z value observed in the mass spectra shown in FIG. 6 where tryptic fragments are denoted $T_n$ where n is the amino acid position;

FIG. 9 is a table of tryptic peptides with m/z value observed in the mass spectra shown in FIG. 8 where tryptic fragments are denoted $T_n$ where n is the amino acid position;

FIG. 11 is a table of the tryptic peptides with m/z value observed in the mass spectra shown in FIG. 10 where tryptic fragments are denoted $T_n$ where n is the amino acid position;

FIG. 14 is a table of tryptic peptides with m/z value observed in the mass spectra shown in FIG. 13 where tryptic fragments are denoted $T_n$ where n is the amino acid position;

FIG. 22 is a table of peptides with m/z value observed in nano-ESI for the in-solution Lys-C digestion of cytochrome c where peptide fragments are denoted $T_n$ where n is the peptide position;

FIG. 23 is a table of peptides with m/z value observed in nano-ESI for the in-solution trypsin digestion of cytochrome c where peptide fragments are denoted $T_n$ where n is the peptide position;

FIG. 24 is a table of peptides with m/z value observed in nano-ESI for the in-solution Tryspin/Lys-C digestion of cytochrome c where peptide fragments are denoted $T_n$ where n is the amino acid position;

FIG. 25 is a table of peptides with m/z value observed in nano-ESI for the in-solution Lys-C digestion of apomyoglobin where peptides are denoted $T_n$ where n is the amino acid position;

FIG. 26 is a table of peptides with m/z value observed in nano-ESI for the in-solution trypsin digestion of apomyoglobin where tryptic fragments are denoted $T_n$ where n is the amino acid position;

FIG. 27 is a table of peptides with m/z value observed in nano-ESI for the in-solution Tryspin/Lys-C digestion of apomyoglobin where peptides are denoted $T_n$ where n is the amino acid position;

DETAILED DESCRIPTION OF THE PREFERRED EMBODIMENTS

Figure 1:
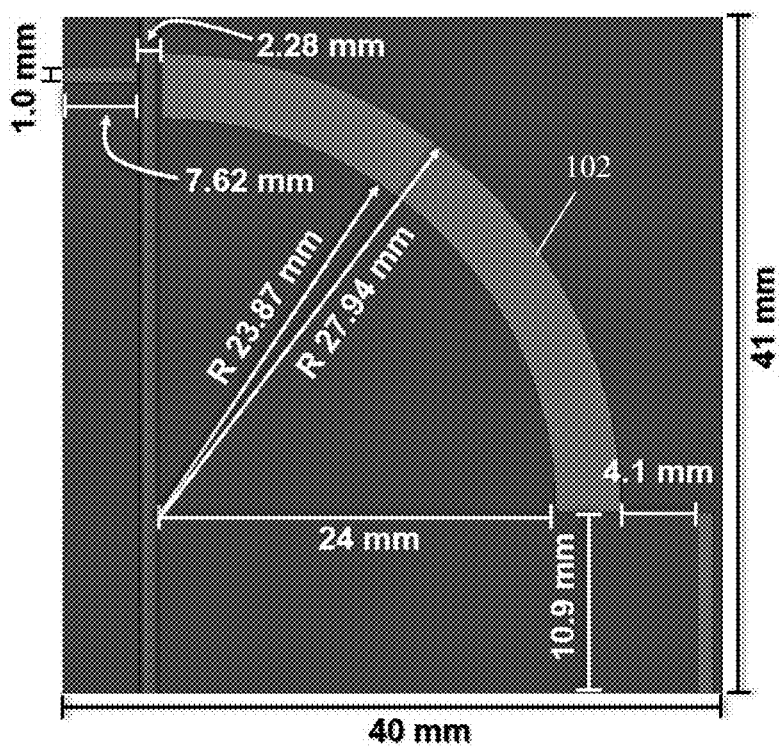
FIG. 1 is schematic view of a microwave microstrip resonator apparatus in accordance with an aspect of the present invention.
Figure 2:
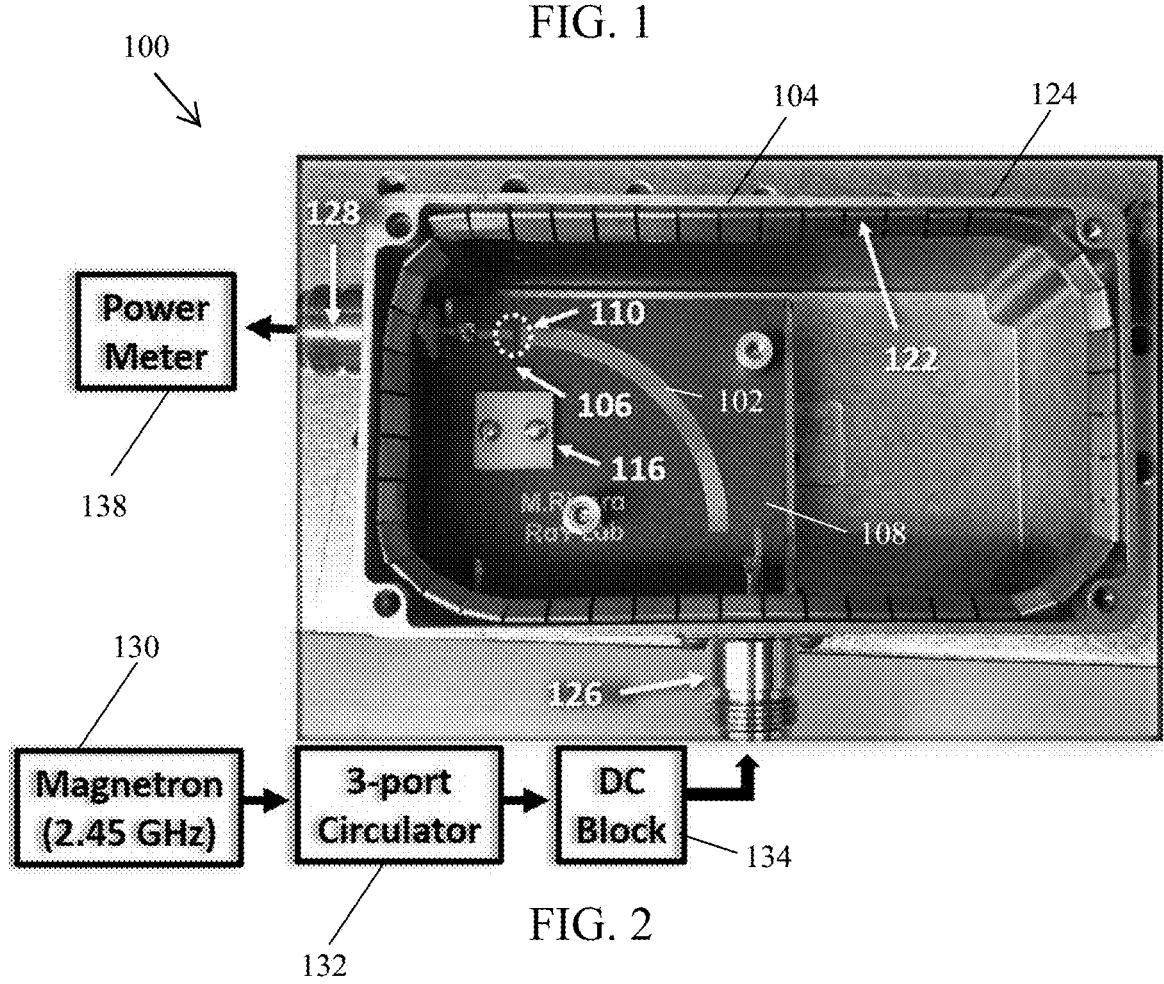
FIG. 2 is a top photographic view of the microwave microstrip resonator apparatus shown in FIG. 1.

Turning now to the figures, with particular reference to FIGS. 1 and 2, an embodiment of a microwave HW microstrip resonator apparatus 100 in accordance with an aspect of the present invention generally includes a microwave resonator 102 within a housing 104. Housing 104 may be constructed of any suitable material, such as but without limitation to aluminum. Resonator 102 may be constructed using a lamination/etching process, such as for example, from a copper clad Rogers Corporation RT/Duroid® 5870 laminated board with a dielectric and dielectric thickness of 2.33 and 0.79 mm, respectively. It should be noted by those skilled in the art that the length and width of resonator 102 were selected to satisfy $\lambda/2$ for a nominal resonant frequency of 2.45 GHz, with anti-nodes located at each end. Alternative geometries may be utilized depending upon the desired frequency.

Figure 3:
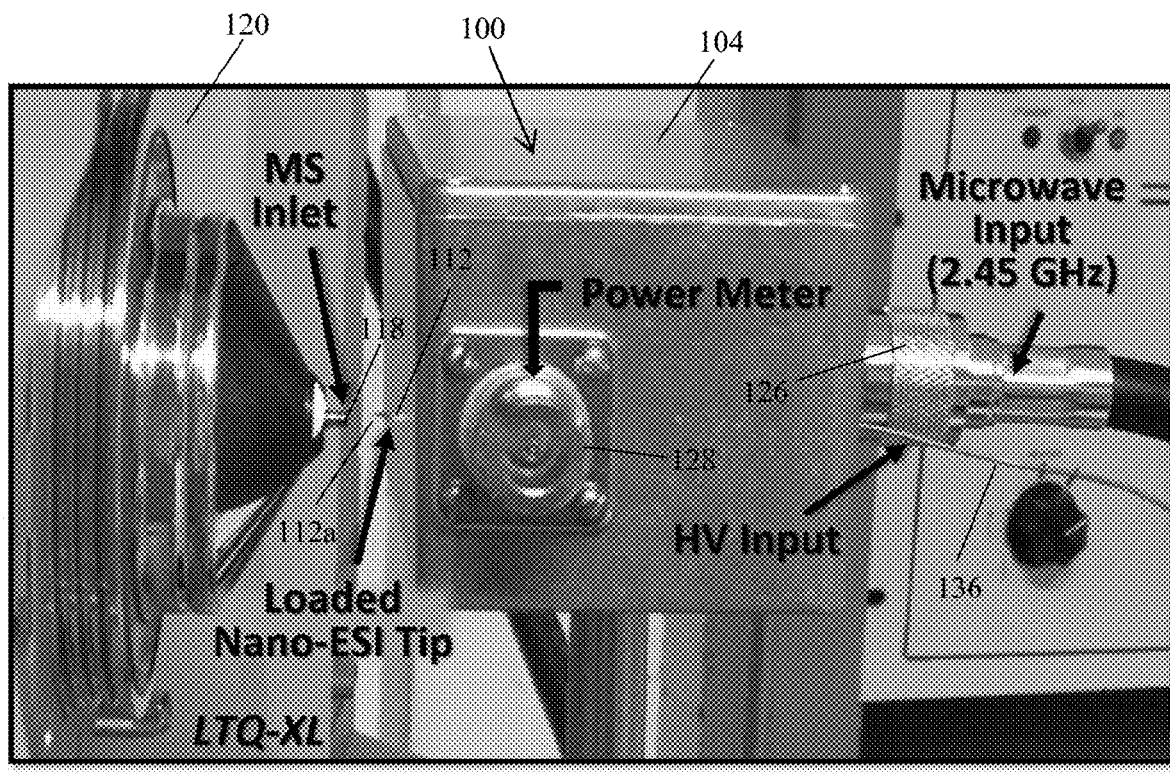
FIG. 3 is a side view of the microwave microstrip resonator apparatus shown in FIG. 2 mounted onto a mass spectrometer.

A groove 106 may be defined within the dielectric material 108 of resonator 102. Groove 106 is configured to lie along a region of high electric field within a capacitive gap 110. Groove 106 may be dimensioned to receive and position a reaction vessel 112 (e.g. capillary, electrospray emitter tip or nano-electrospray emitter tip) in microstrip 114 of resonator 102 (see also FIG. 3). A non-conductive (e.g., Teflon) holder 116 may be included within housing 104 to keep the capillary 112 in place during use. As shown in FIG. 3, a distal end 112a of capillary 112 may be position proximate to an inlet 118 of a mass spectrometer 120. Housing 104 may include a copper gasket 122 attached along the upper internal surface of housing walls 124 in order to minimize microwave radiation spreading beyond the confines of housing 104.

With continued reference to FIGS. 1 and 2, apparatus 100 includes two main lines: an input line 126 to feed power to the microstrip resonator 102 and an output line 128 for testing and calibration purposes. In accordance with an exemplary system, a magnetron microwave power supply (MicroNow, Inc.) 130 may be used to supply a 2.45 GHz microwave waveform through a 3-port circulator 132. The 3-port circulator 132 acts as a directional coupler to ensure microwave power is not reflected back into the magnetron source in case of high reflected powers due to a poor impedance match, in which case energy is instead directed into a 50 ohm load. A direct current (DC) block (Pasternak, 10 MHz-18 GHz) 134 may also be attached in line to the RF coax output power terminal of input line 126 to protect supply 130 from any high DC potentials that may accidently be applied from the nanoESI voltage source 136 (see FIG. 3). A microwave power meter (Hewlett-Packard Company) 138 may be connected to output line 124 in order to calibrate forward and reverse power levels. All the experiments were carried out feeding the system with a net forward power of 20 W.

Figure 4:
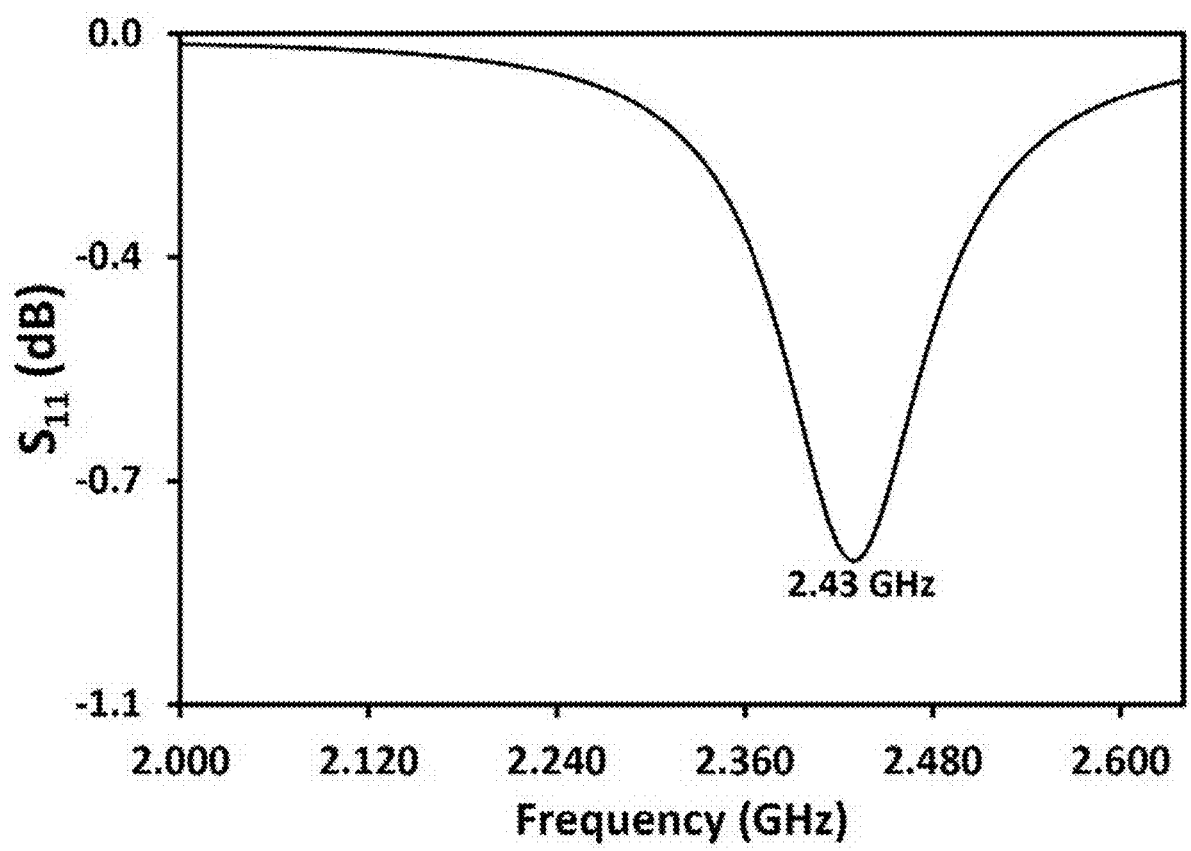
FIG. 4 is an S-Plot of the microstrip resonator apparatus shown in FIG. 2.

All the electromagnetic simulations were performed using Ansys HFSS 3D simulation software. The exemplary microstrip resonator 102 shown and described above was found to resonate at a frequency of 2.43 GHz with a return loss of −0.826 dB as determined by the S-plot simulation results shown in FIG. 4. Exemplary microstrip resonator 102 also showed minimal variability in both the resonating frequency and return loss upon incorporation of materials between capacitive gap 110, however changes in the electric field distribution were observed.

Figure 5:
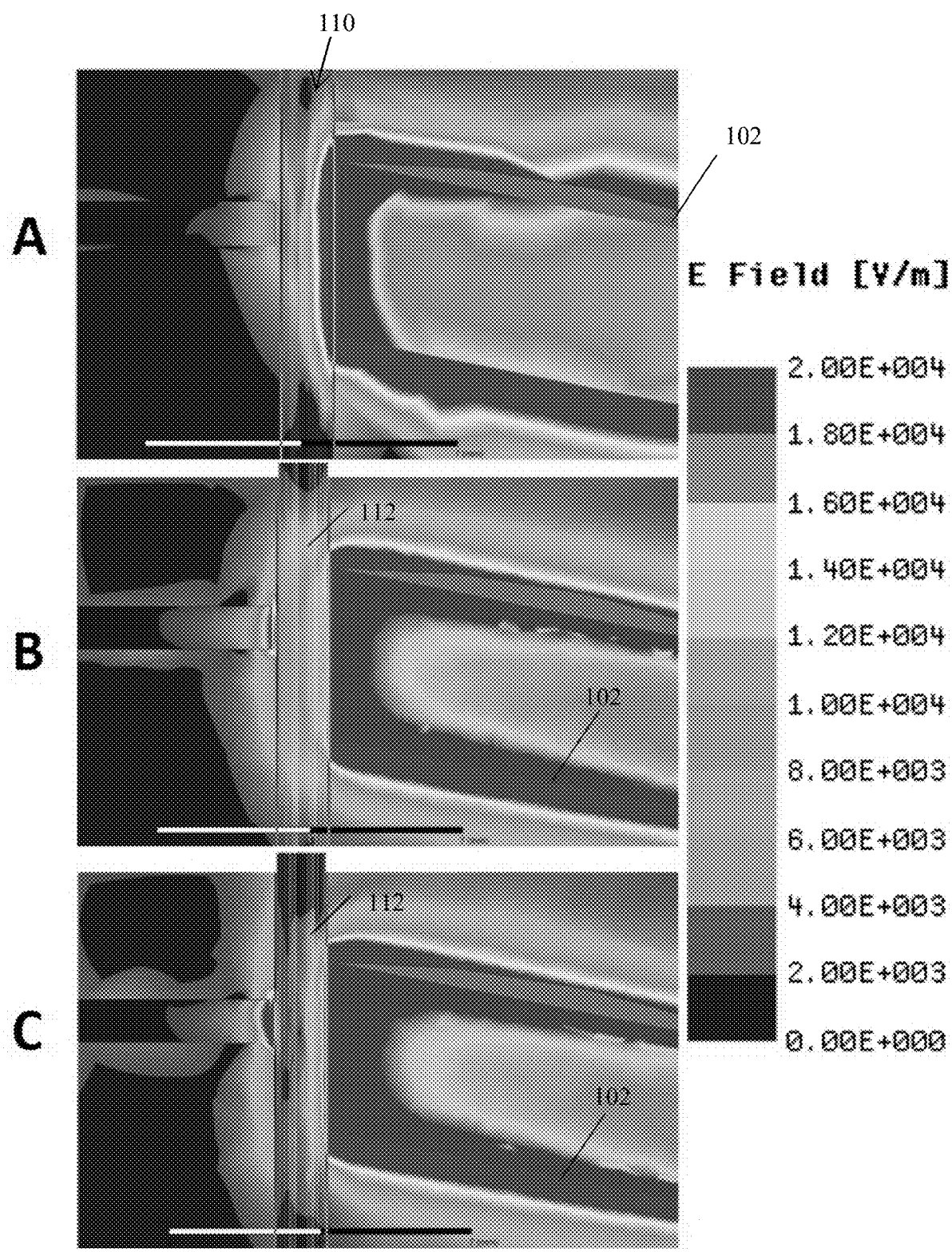
FIG. 5 shows simulations of the electric field distribution along the capillary gap of the microstrip resonator apparatus shown in FIG. 2, with A) having no capillary in the gap, B) having an unfilled capillary in the gap, and C) having a water filled capillary in the gap.

Without being tied to any one particular theory, the fact that no significant changes were observed in the resonating frequency and return loss of the systems is an indication of the stability of the microstrip resonator upon material or sample loading. Exemplary microstrip resonator 102 showed increased electric field focusing upon sample loading between the capacitive gap 110 which likely indicates localized heat generation. This phenomenon was studied by simulating three different scenarios in which the microstrip resonator contained no quartz capillary, an empty quartz capillary and quartz capillary filled with water, respectively (see FIGS. 5A-5C). As shown in FIG. 5A, the electric field was observed to propagate along capacitive gap 110 when no capillary was present, concentrating the most to the edges of the capacitor, an indication of microwave skin effect. As shown in FIG. 5B, a similar behavior was observed when an empty capillary 112 was positioned in resonator 102, but with an increased intensity of the electric field at the edges of the capacitor. With reference to FIG. 5C, the electric field distribution in capillary 112 filled with water showed increased electric field at the edges of the capacitor, but diminished intensity inside the capillary, likely due to the depolarizing properties of water. Based upon these results, the presence of polar solvent generates intense electric fields in situ due to dielectric heating.

Representative Examples

Microwave-Assisted Trypsin Digestions of Proteins in the HW Microstrip Resonator The capabilities of the microstrip HW resonator apparatus 100 as a reactor for microwave-assisted digestion of proteins was assessed. For these purposes, trypsin digestion of myoglobin, β-casein, cytochrome c and ubiquitin (from Sigma-Aldrich) were prepared as individual 20 μM standards in 80/20 (v/v) water/acetonitrile (ACN) with 10 mM ammonium bicarbonate ($NH_4HCO_3$, pH 8.0) at an enzyme to substrate ratio of 1:25 (by weight, w/w) were carried out. Trypsin was selected as the proteolytic enzyme due to its easy availability and well-known chemistry. The in-solution digestion samples were directly injected into a nanoESI tip laser pulled from quartz capillary (1.0 mm OD) by using a Sutter Instrument Co. (Novato, Calif.) P-2000/G laser-based micropipette puller.

Samples were injected into the tip emitter without further treatment. The sample loaded tip emitter (capillary 112) was positioned along groove 106 of HW microstrip resonator 102. The effect of microwave assisted trypsin digestion of proteins was assessed by irradiating the in-solution digestion sample contained inside capillary 112 with a fixed 20W net power for various times intervals (2, 5 and 10 minutes, respectively) prior to direct nanoESI and mass spectrometry characterization. Microwave fields were introduced to resonator 102 using magnetron high power supply 130 followed by 3-port circulator 132 to direct the field to the load. Distal end 112a of capillary 112 was then located ~0.5 cm from the MS inlet 118 of a LTQ XL (Thermo Fisher Scientific) mass spectrometer 120 and the positive mode nanoESI was sustained by applying 1-2 kV to the sample using high voltage (HV) power supply 136. Microwave power supply 130 was turned off after the desired digestion residence time prior to nanoESI and mass spectra data acquisition. Trypsin conventional digestion (no microwave irradiation) of the proteins at room temperature for 10-20 hours were also performed for comparison purposes. It should be noted that, while the mass analyzer used within the examples is an ion trap, alternative mass analyzers may be used, such as, but not limited to Fourier transform or triple quadrupole mass spectrometers by easily interfacing the dual ion source-resonator system to such analyzers.

Trypsin Digestion of Myoglobin

Figure 6:
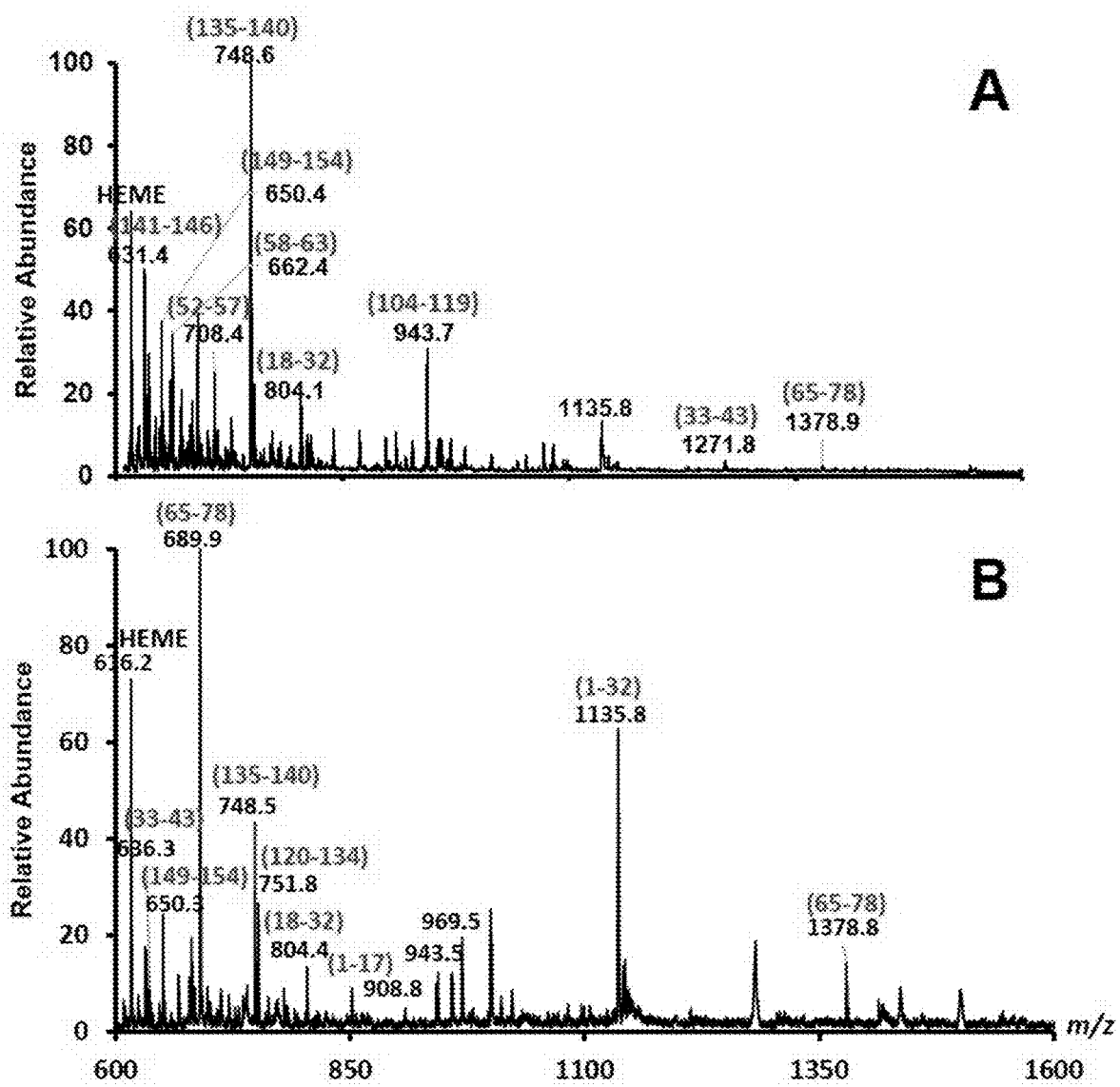
FIG. 6 are mass spectra of a trypsin digestion of myoglobin, with A) showing results of a conventional 10-h digestion, and B) showing the results of microwave-assisted digestion using the microstrip resonator apparatus shown in FIG. 2 for 10-min at 20 W.

Myoglobin was initially used to demonstrate the utility of the microwave-assisted digestion of protein with the HW microstrip resonator. The effect of microwave irradiation within the in-solution digestion of myoglobin contained inside the microcapillary vessel are shown in FIGS. 6A and 6B, with FIG. 6A showing a conventional digestion after 10-hours and FIG. 6B showing microwave-assisted digestion after 10-minutes at 20 W. The microwave irradiation digestion resulted in a protein sequence coverage of 88%. The obtained peptide coverage with microwave-assisted digestion was found to be higher than the one obtained for the conventional digestion protocol (82%). The non-covalently bound heme (m/z=616) was observed in both digestion protocols. Tryptic peptide 33-43 was not observed in the microwave-assisted protocol while the conventional counterpart was missing fragment 120-134. Interestingly, missed cleavage tryptic fragments 1-32, 49-57, 58-64 arise from helical regions within the protein structure, and although absent on the conventional protocol, were observed in the microwave-assisted approach. Overall, a greater number of missed cleavage peptides were observed when using microwave assisted proteolysis. Neither sodiated molecular ion from the protein nor peptide fragments were observed with our digestion protocol.

Trypsin Digestion of Cytochrome c

Figure 8:
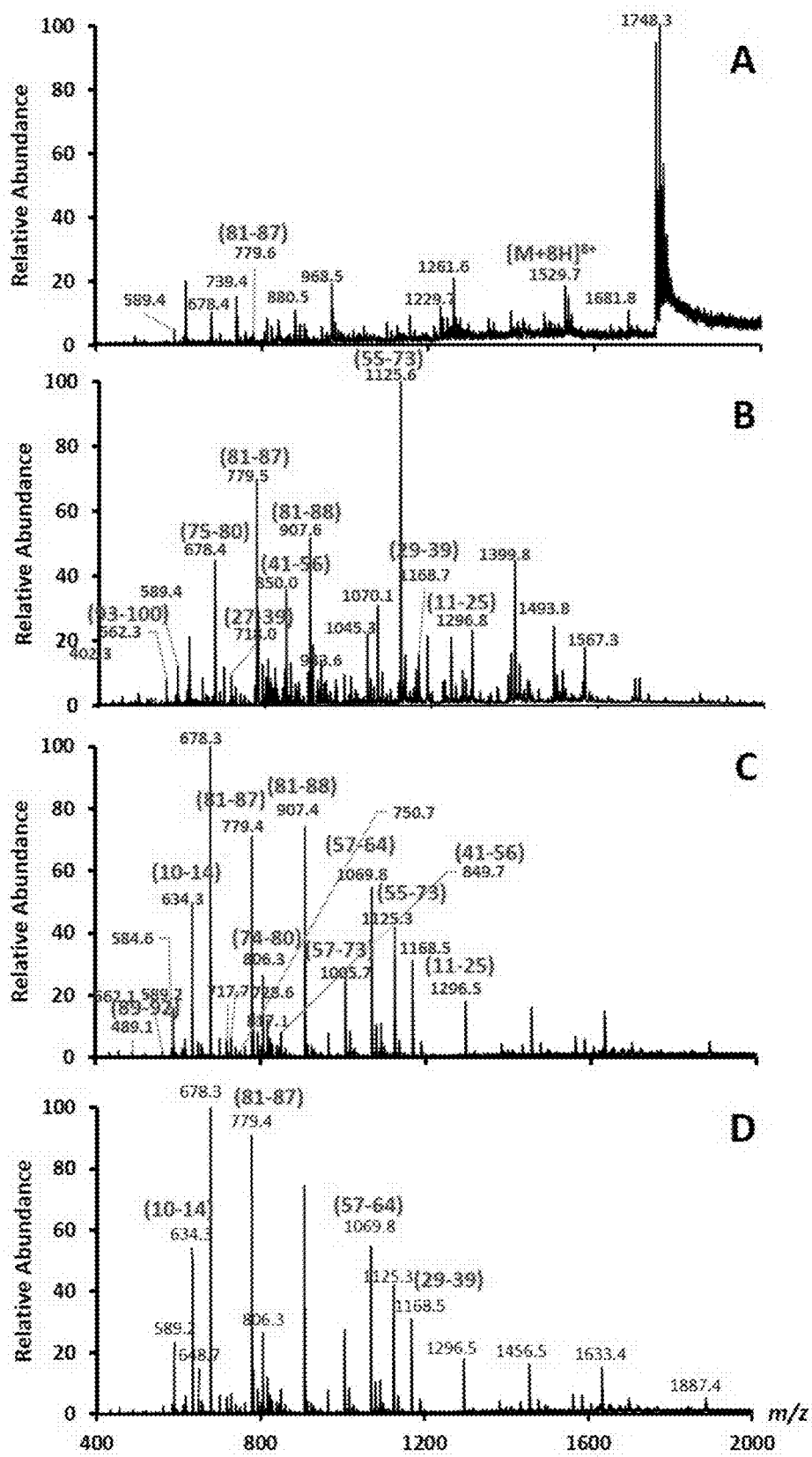
FIG. 8 are mass spectra of a trypsin digestion of cytochrome c, with A) showing the results of microwave-assisted digestion using the microstrip resonator apparatus shown in FIG. 2 for 2-min at 20 W, B) for 5-min at 20 W, C) for 10-min at 20 W, and D) showing results of a conventional 20-h digestion.

With reference to FIGS. 8A-8C, cytochrome c was also used to evaluate the microstrip resonator 102. Similarly, the in-solution digestion sample contained inside the nano-ESI tip was irradiated with 20 W microwave power for 2-min (FIG. 8A), 5-min (FIG. 8B) and 10-min (FIG. 8C), respectively. Immediately after each residence time, nano-ESI was conducted by applying 1.8 kV to the sample and subsequent mass spectra were recorded. Microwave assisted digestion resulted in protein sequence coverages of 17%, 50%, and 87% at irradiation times of 2 min, 5 min, and 10-min, respectively. The obtained peptide coverage with just 10-min of microwave-assisted digestion (87%) was found to be highly comparable to the one obtained for the conventional digestion protocol (95%) (see FIG. 9). The presence of the peptide sequence (15-23) containing the covalently bound protein heme c group was not detected with microwave irradiation. The tri-peptide GGK (residues 22-26) contained within the secondary structure motif of cytochrome c (alpha-helix to beta-strand), was not observed in the conventional protocol, but appeared in the microwave-assisted digestion. Similarly, to the myoglobin digestion results, greater number of missed cleavage peptides were observed when using microwave assisted proteolysis and multiple charges of the peptides ions were also observed.

Trypsin Digestion of β-Casein

Figure 10:
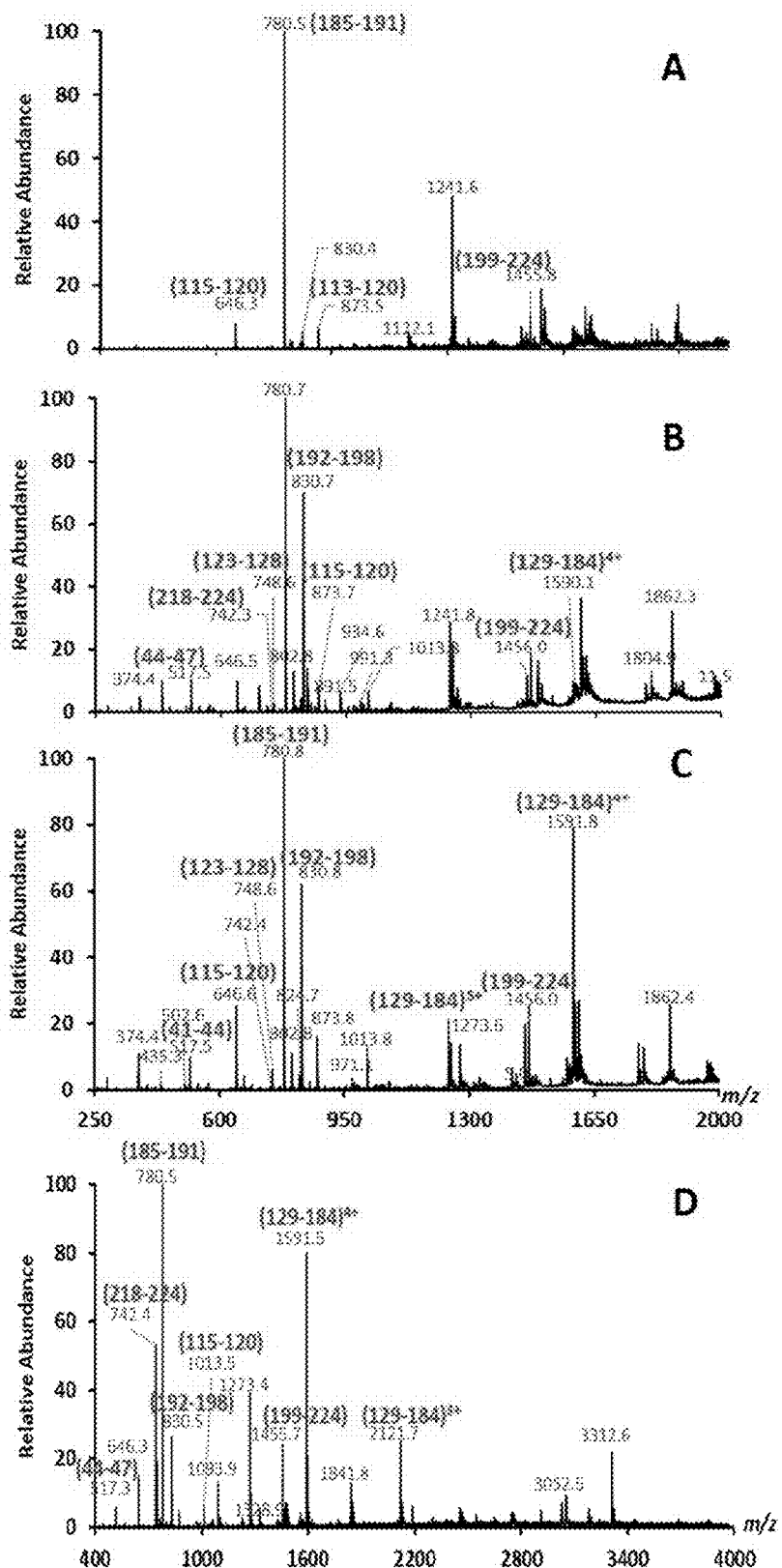
FIG. 10 are mass spectra of a trypsin digestion of β-casein, with A) showing the results of microwave-assisted digestion using the microstrip resonator apparatus shown in FIG. 2 for 2-min at 20 W, B) for 5-min at 20 W, C) for 10-min at 20 W, and D) showing results of a conventional 10-h digestion.

The effect of microwave-assisted digestion on a phosphoprotein was assessed by the digestion β-casein. As shown in FIGS. 10A-10C, microwave-assisted digestion at 2-min (FIG. 10A), 10-min (FIG. 10B) and 15-min (FIG. 10C) generated peptide sequence coverage of 10%, 27%, and 53%, respectively, which is highly comparable with the coverage obtained with the 10-h conventional digestion protocols (53%) as shown in FIG. 11. An overall higher peptide ion abundance together with an increased sequence coverage was observed upon longer residence times with microwave exposure. A long tryptic peptide sequence (199-224) was observed in the conventional digestion protocol, but not in the microwave-assisted digestion, while sequences 41-44 and 122-128 were not observed in the conventional approach but were observed in the microwave-assisted digestion. Interestingly, the latter protein segments have high charge frequency and average hydrophobicity, respectively, and have been reported to have some temperature dependence. Several missed-cleavage peptides were also observed using both approaches. No neutral losses of phosphoric acid ($H_3PO_4$) associated to phosphorylated peptides were identified in microwave-assisted nor conventional digestion, although other studies recommend the detection of tryptic phosphopeptides in negative mode under basic conditions, which may change detectability.

Trypsin Digestion of Ubiquitin

Figure 12:
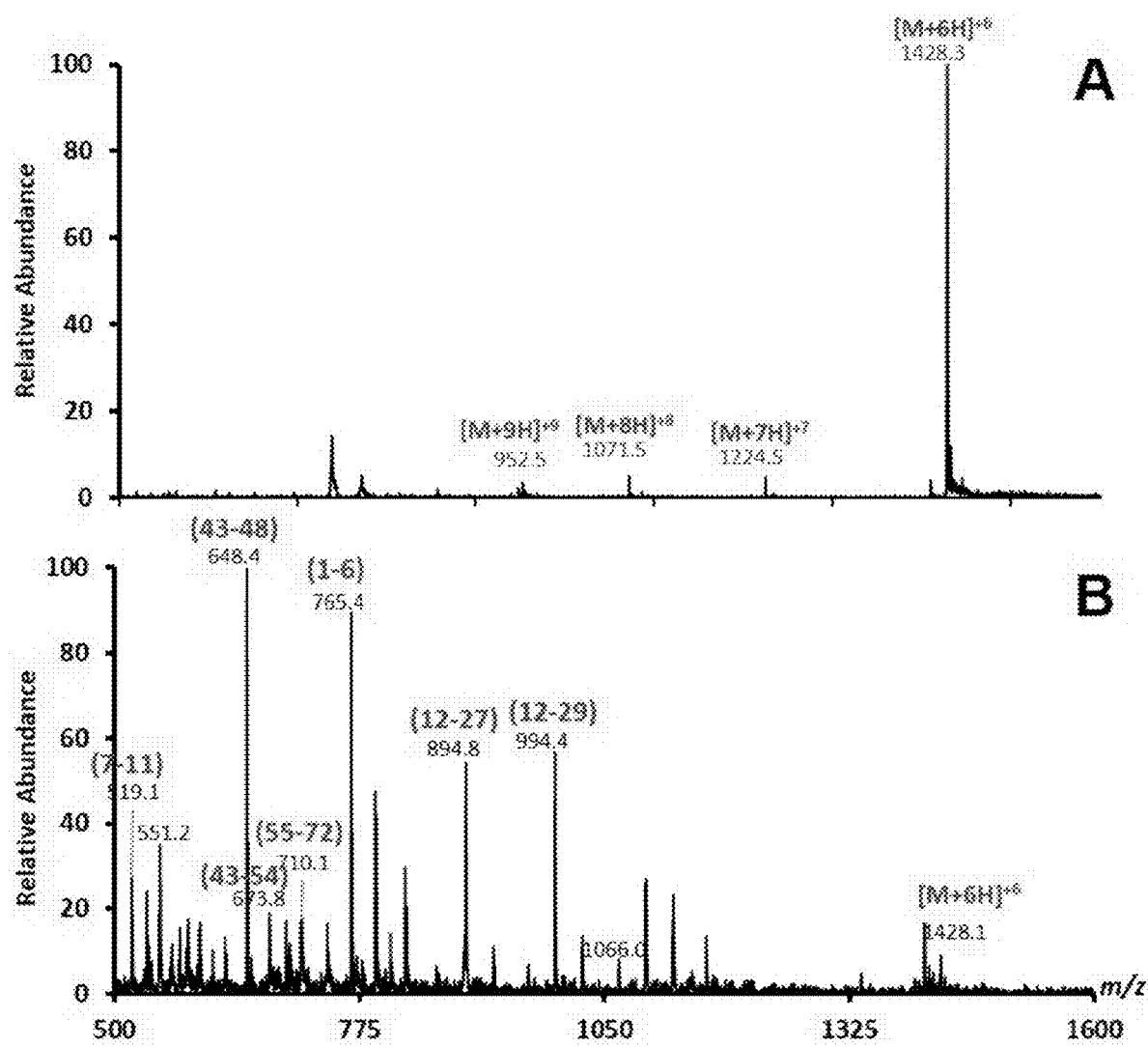
FIG. 12 are mass spectra of a trypsin digestion of bovine ubiquitin, with A) showing results of a conventional 10-min digestion, and B) showing the results of microwave-assisted digestion using the microstrip resonator apparatus shown in FIG. 2 for 10-min at 20 W.
Figure 13:
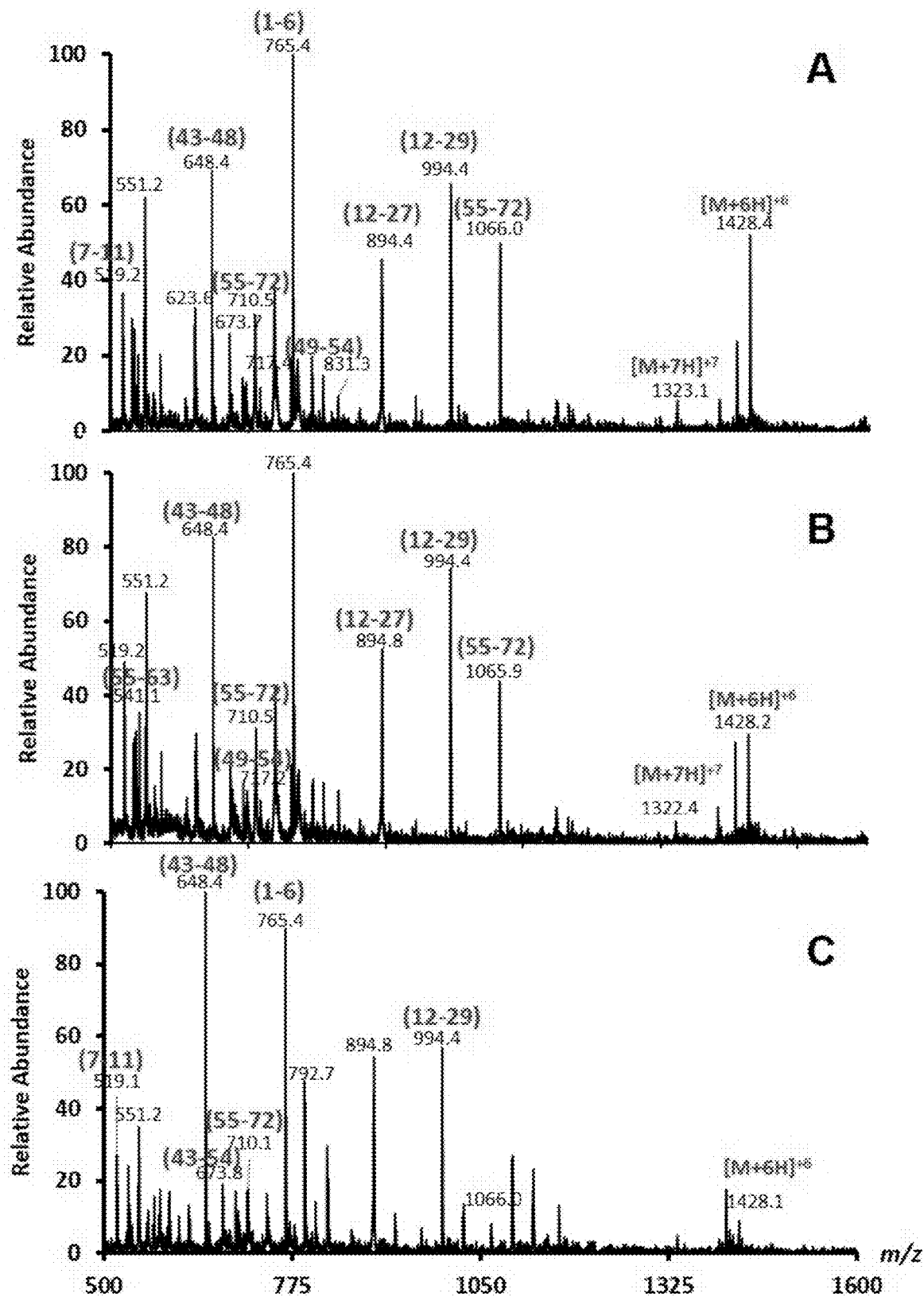
FIG. 13 are mass spectra of a trypsin digestion of bovine ubiquitin, with A) showing the results of microwave-assisted digestion using the microstrip resonator apparatus shown in FIG. 2 for 5-min at 20 W, B) for 10-min at 20 W, and C) for 15-min at 20 W.

The effect of microwave irradiation in the in-solution digestion of a tightly-folded protein was studied by using bovine ubiquitin. Bovine ubiquitin is a tightly-folded protein which is resistant to denaturation and it is thought to undergo enhanced proteolysis under microwave irradiation. FIGS. 12A and 12B illustrate the effect of 10-min digestion with fixed 20 W net microwave power FIG. 12B compared to the mass spectrum of 10-min conventional digestion of bovine ubiquitin FIG. 12A. While the mass spectrum of 10-min conventional trypsin digestion only shows the multiple charge peaks of protonated ubiquitin, the microwave-assisted digestion protocol exhibited significant enhancement in protein sequence coverage. After only 5-min of microwave irradiation a protein sequence coverage of 75% was achieved. Comparable sequence coverages were achieved for 10 min and 15-min of microwave irradiation (83 and 94%, respectively) with no significant denaturation (see FIGS. 13 and 14). Mostly shorter peptide sequences were missed. Tightly folded proteins are known to require long digestion times for adequate enzymatic proteolysis, the microwave-assisted protocol showed great improvement in ubiquitin digestion rates reducing the required times from hours to minutes.

Figure 15:
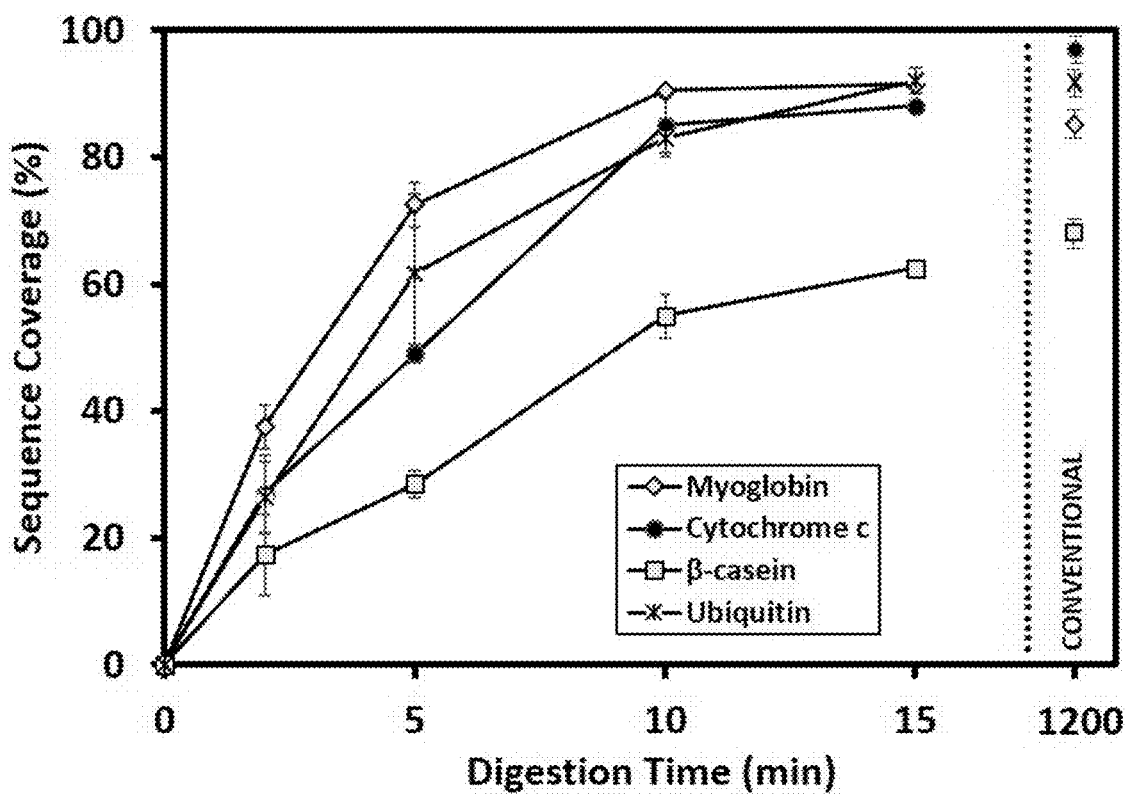
FIG. 15 are plots shown the rate of microwave-assisted trypsin digestion of myoglobin, cytochrome c, β-casein, and ubiquitin after different residence time of microwave irradiation at 20 W.

As shown in FIG. 15, microwave HW microstrip resonator apparatus 100 is an efficient approach for inline protein digestion while also reducing the amount of sample and overall sample handling required. It was observed that the peptide sequence coverage increased upon increments in microwave irradiation times showing a greater effect in those proteins resistant to denaturation which might represent a great advantage in proteomics. Generally, peptide sequence coverage highly comparable to those obtained with lengthy conventional protocols were achieved at much faster digestion times (see FIG. 15).

Figure 16A:
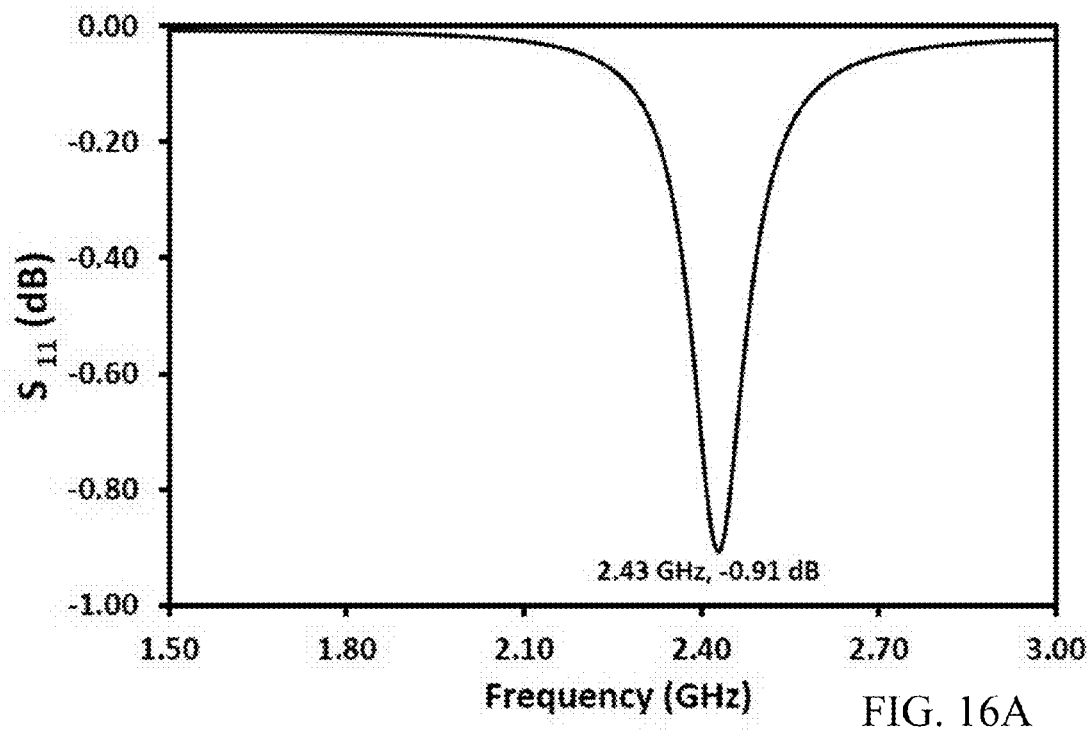
FIG. 16A is an S-Plot of another microwave microstrip resonator apparatus in accordance with an aspect of the present invention having an output conductor with a length of 1-cm.
Figure 16B:
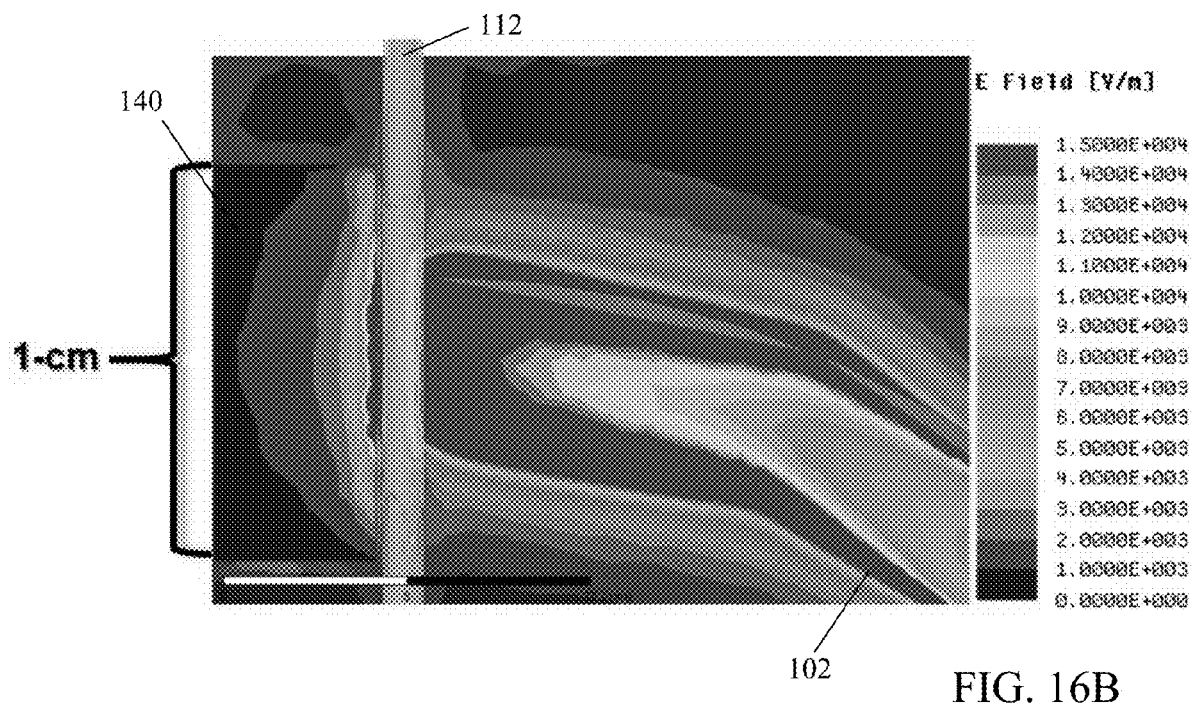
FIG. 16B is a simulation of the electric field distribution along the capillary gap of the microstrip resonator apparatus having an output conductor with a length of 1-cm and with a water filled capillary in the gap.

FIGS. 16A and 16B shows a simulation of the electric field distribution along capacitive gap 110' of microwave resonator 102' with longer output conductor 140 with a capillary 112 filled with water (FIG. 16A) with FIG. 16B shown an S-Plot of microwave resonator 102' with an output conductor with length of 1 cm (as opposed to 1 mm as shown and described above).

Figure 17:
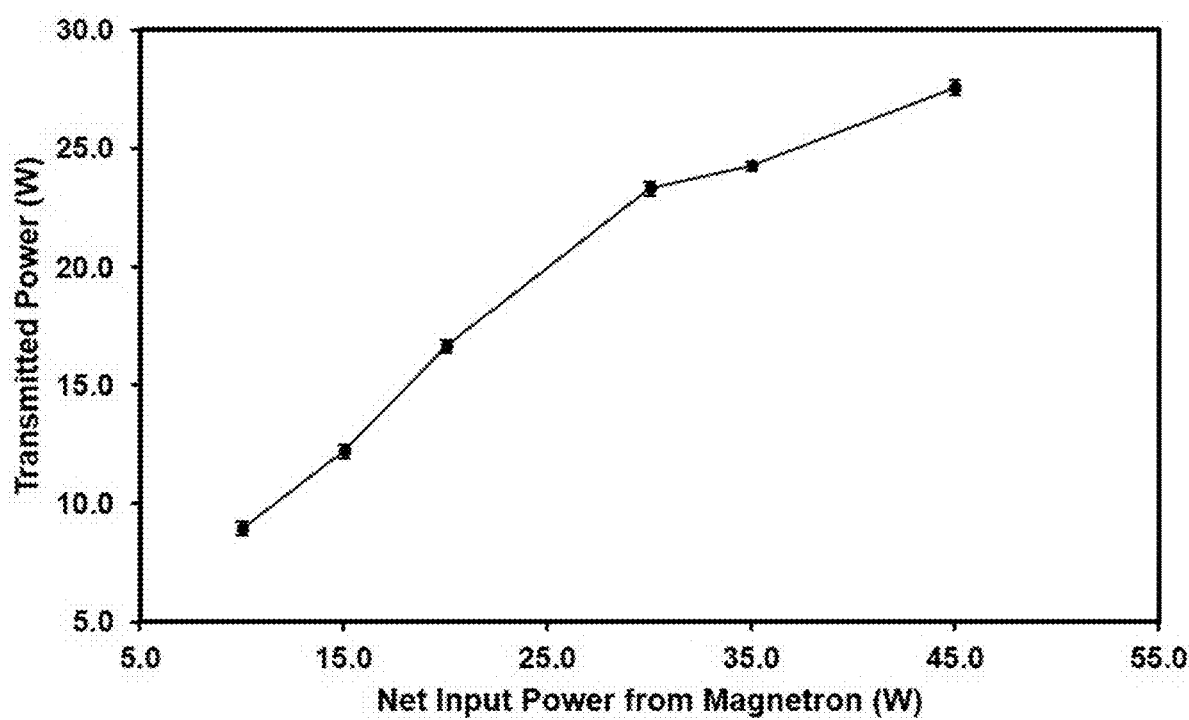
FIG. 17 is a plot of microwave transmitted power of the microwave microstrip resonator apparatus shown in FIG. 1 as a function net input power.

FIG. 17 shows microwave transmitted power output as function of net input power. As can be seen, a direct relation between net input and transmitted power is observed with a slight increase in power loss as function of input power. Note that tests were performed with the empty resonator.

Microwave-Assisted Immobilized Enzymatic Digestion

Figure 18:
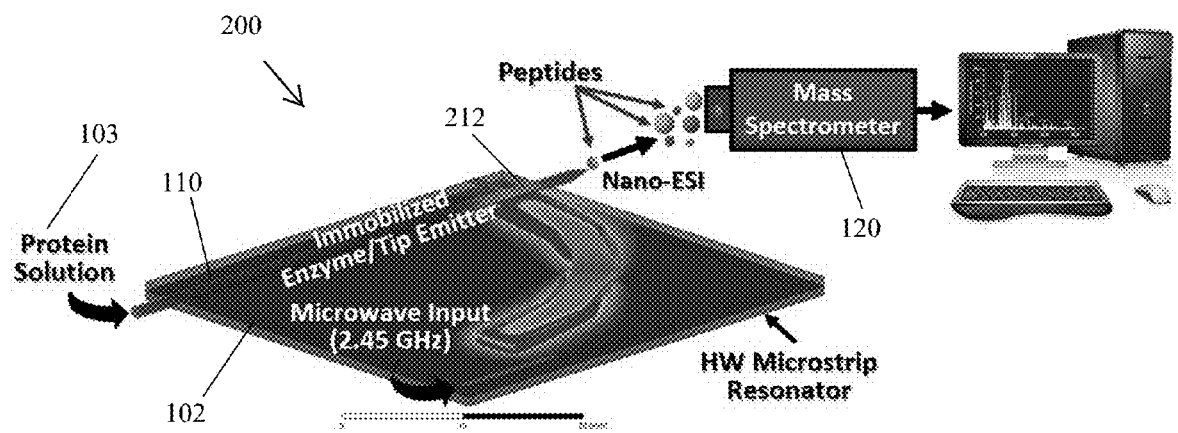
FIG. 18 is a schematic view of an immobilized enzyme microwave-assisted system in accordance with an aspect of the present invention.

In accordance with another aspect of the present invention, enzymes may also be immobilized on structures such as capillary surfaces or particles in order to create a reactor bed 213 for proteolysis and to accelerate protein digestion. As shown in FIG. 18, system 200 may provide the advantages of enzyme reusability, reduced enzymatic autolysis (due to restriction of enzyme movability), increased enzyme concentration per volume area and reduced digestion times. Immobilized enzymatic reactor 212 may be combined with system 200 to expose the reactor beds 213 within reactor 212 to the focused microwave field generated by resonator 102. In one aspect of the invention, reactor 212 may be fabricated by immobilizing enzyme 214 within the tip 216 of the reactor 212. See reactor 212a shown in FIG. 19(a). Alternatively, or additionally, enzyme 214 may be placed as a bed 218 of enzyme-covered particles 220 within reactor 212 as a flow-through reactor bed. See reactor 212b shown in FIG. 19(b). As shown in FIG. 18, by incorporating a tip emitter (reactor 212 functionalized with immobilized enzyme 214) between the capacitive gap 110 of the microstrip resonator 102, protein solution 103 can be digested as the solution flows through the tip. In-reactor digestion is beneficial in proteomic workflows as it allows for rapid reaction completion using small volumes. The small, contained volume of protein solution 103 in reactor 212 are also able to be quickly heated when using the microwave resonator 102 such that a rapid reaction can be achieved suitable for online mass spectrometry analysis.

As discussed above, microwave heating using resonator 102 is strongly dependent upon the dielectric constant of the composite material used in fabricating the resonator. Susceptibility to localized heating by choice of materials based on tangent loss value is also possible. Thus, in accordance with an aspect of the present invention, a wide variety of microwave absorbing materials, such as, but not limited to, alumina, $TiO_2$ nanoparticles, magnetite/ferrite beads, and other materials, may be used with resonator 102. As will be discussed in greater detail below, the selection of various materials permits sections or volumes of the reactor, such as reactor 212 to be heated at different rates based on relative energy absorption, allowing for localized or staged temperature control.

Figure 19:
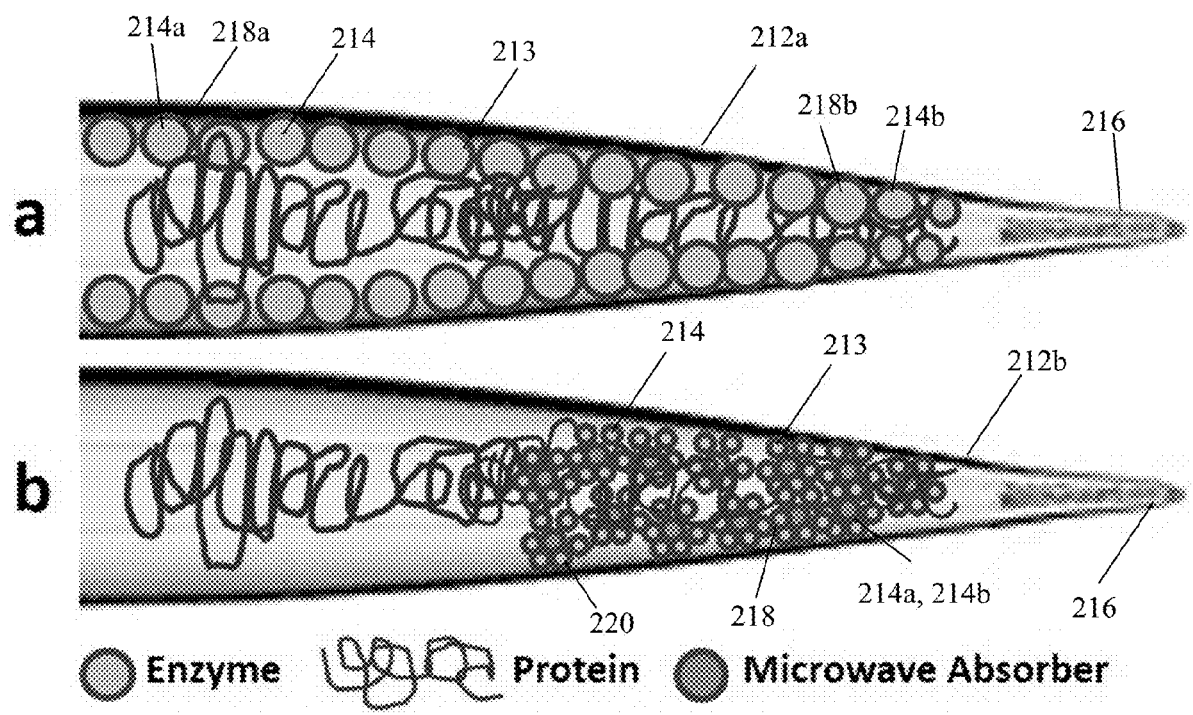
FIG. 19 is a schematic view of immobilized enzyme for enzymatic digestion with the enzyme covalently bound to the silica support within the capillary inner walls (a) or attached through adsorption on a microwave absorber material (b)

By way of example and without limitation thereto, localized temperature control may use a packed bed of material as a reaction volume, such as bed 218 in FIG. 19(b). Packed-bed reactor 212b composed of beads, nanoparticles, colloids, or other materials 218 increase the total surface interaction area and reduce diffusion time of substrate (e.g., protein solution 103) to the site of enzyme reaction (e.g., enzyme 214). Packing materials can also be selected for tangent dielectric loss value and microwave absorption. For example, in one embodiment magnetic microspheres of high dielectric loss may permit local heating of packing bed 218. Magnetic media may also allow for subsequent reuse and recovery. Thus, dielectric heating can be favorably applied to those sites responsible for protein/enzyme interactions, and the surface-to-volume ratio of the reactor may also be greatly increased, thus improving efficiency of immobilized enzyme digestion.

Chromatographic Separations/Flow Injection Analysis/Flow through System

Figure 18A:
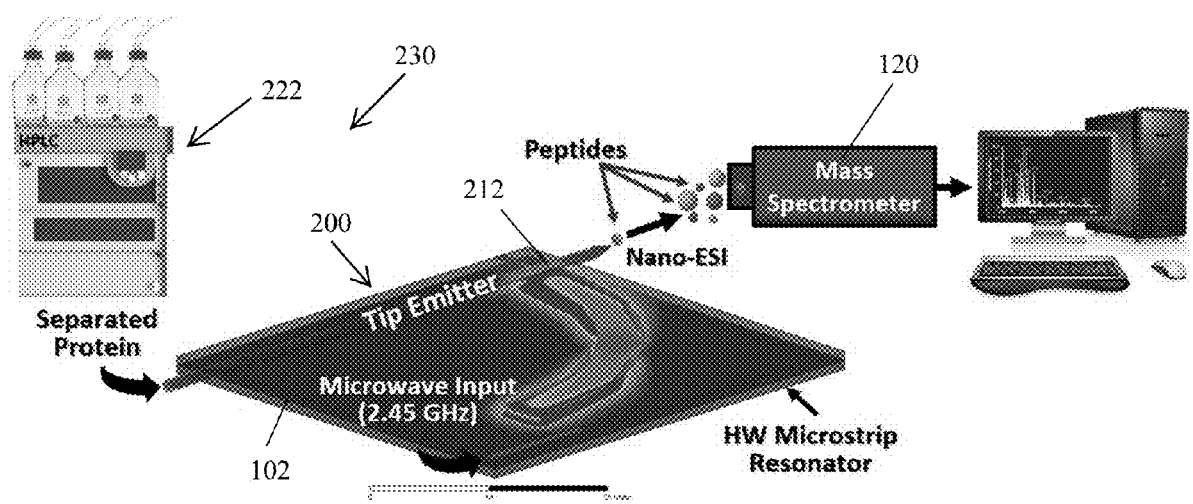
FIG. 18A is a schematic view of an exemplary microwave-assisted system setup coupled to liquid chromatography system for multidimensional analysis.

Moreover, high efficiency digestion and high enzyme-to-protein ratios may decrease proteolysis times and permit rapid digestions for flow-through types of applications, such as when coupling system 200 with a continuous flow system 222, such as liquid chromatography, flow injection analysis, capillary electrophoresis, multidimensional separations, or other separation approaches. See FIG. 18A. As a result, complex samples containing multiple proteins can be separated and then digested inline in a continuous fashion within the separation system/immobilized enzyme reactor/microwave resonator system 222/212/200 (collectively system 230). By way of example, proteins and peptides from complex mixtures are often isolated and analyzed by chemical or physical separation approaches combined with mass spectrometry, such as liquid chromatography mass spectrometry (LC/MS). In one aspect of the invention, complex samples 103 containing multiple proteins can first be separated using liquid chromatograph (LC) 222 before being selectively digested inline within microwave reactor 212b, followed by analysis in real-time by mass spectrometer 120.

Real-time power modulation can also provide a feedback control over abundance and types of peptide fragments observed within the mass spectra, which can be particularly useful if included in a flow-through reactor system 230 using an immobilized enzyme or packed bed reaction area within an emitter tip 212a, 212b. Additionally, modulation of proteolysis reactions on a chromatographic timescale can provide supplemental information to chromatographic separations, allowing intact proteins to be observed and then digested during the separation. In one example, proteins or peptides separated by the chemical separation step (LC) can be digested (in reactor 212) for post-translational modification (PTM) identification. As each protein or peptide emerges from the primary separation (LC 222), it can be modified by enzymatic reaction within reactor 212 in order to identify the PTM. For example, glycosylated peptide fragments can be easily identified by in-line flow-through enzyme cleavage of the sugar modification in a real-time manner. It should also be further noted that microwave resonator 102 can also be included prior to a chemical separation (LC 222), digesting the mixture of proteins before separation.

Multiple Enzyme Digestion

In accordance with another aspect of the present invention, a multiple enzyme proteomic digestion strategy provides improved sequence coverage of a protein structure by enhanced digestion and multiple-orthogonal proteolytic cleavage sites, increasing the chances of modification site identification and protein elucidation. Complementary selectivity of enzymes generates more peptides within the preferable mass range for peptide identification. Multiple enzymes (e.g., 214a, 214b) can be used within reactor 212 and may be positioned either in series (214a in a bed 218a before enzyme 214b in bed 218b) or in combination (enzymes 214a, 214b distributed randomly within a bed 218). A variety of enzymes can be employed within microwave reactor 212, and in accordance with one aspect, may include enzymes having high thermal stability or a thermophilic nature. A non-limiting list of enzymes includes, for example, endoglycosidases, glucosidase (e.g. β-GAL (galactosidase) and α-GAL), carboxylesterase, and xylanases, as well as many others.

The effect of microwave field on different exemplary proteolytic enzymes (endoproteinase Lys-C and trypsin) and different exemplary proteins (cytochrome c (FIG. 20—spectra series a) and apomyoglobin (FIG. 21—spectra series b)) is shown wherein microwave resonator 102 had a net power of 20 W (spectra 2-4) and a conventional 10-minute digestion at room temperature (spectra a1, b1). Endoproteinase Lys-C cleaves proteins on the C-terminal side of lysine residues (spectra a2, b2) while trypsin cleaves proteins on the C-terminal side of lysine and arginine residues (spectra a3, b3). A digestion using a combination of Trypsin/Lys-C is shown in spectra a4, b4. A complete list of all observed peptides at different incubations times with and without microwave irradiation are tabulated in FIGS. 22-24 for apomyoglobin and FIGS. 25-27 for cytochrome c.

Figure 20:
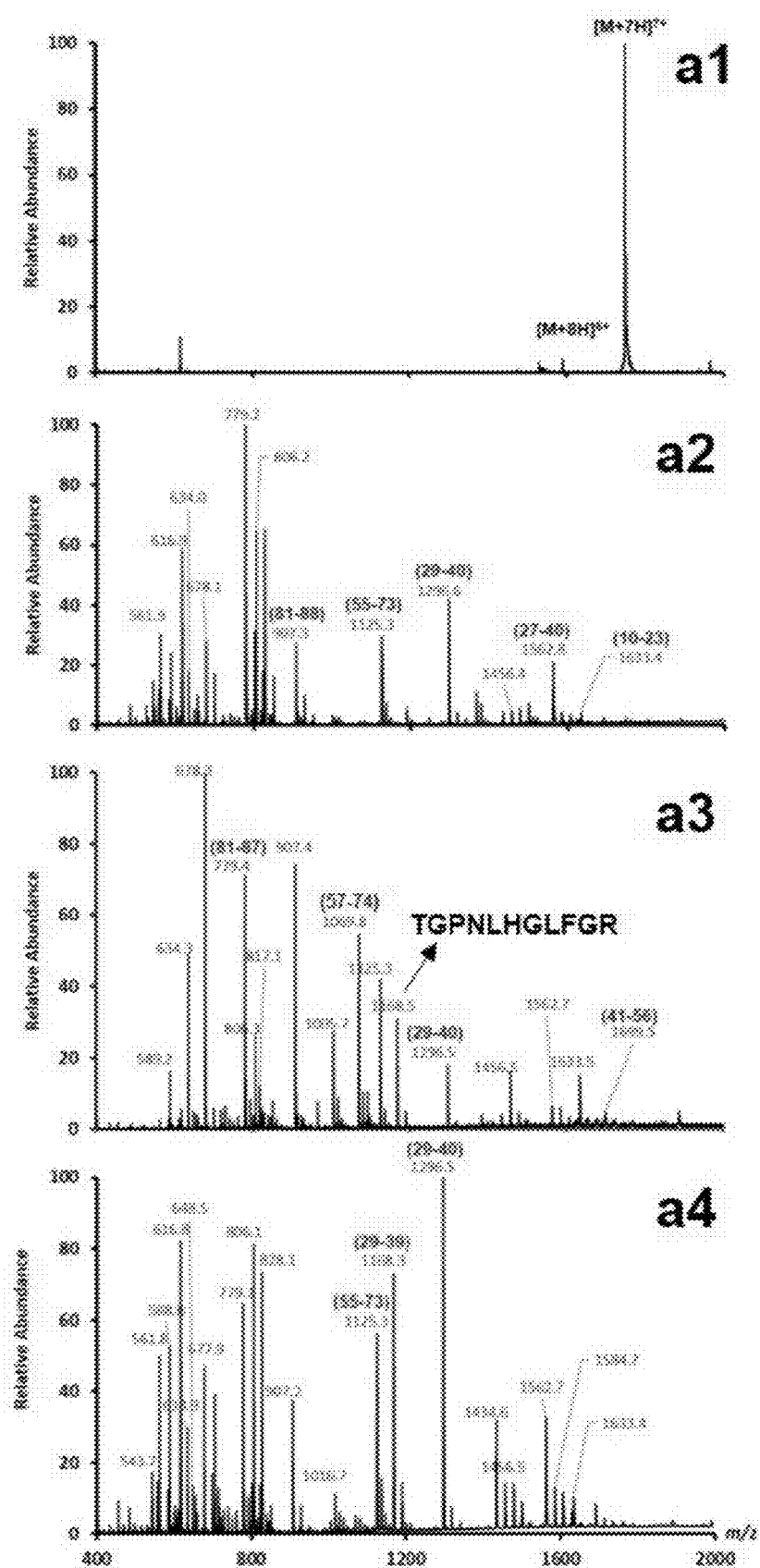
FIG. 20 shows mass spectra of multiple enzyme digestions of cytochrome c with spectra of the digestion products after 10-min conventional digestion at room temperature (a1) and 10-min microwave-assisted digestion at 20 W net power within the microstrip resonator with endoproteinase Lys-c (a2), trypsin (a3) and a combination of Trypsin/Lys-C (a4)
Figure 21:
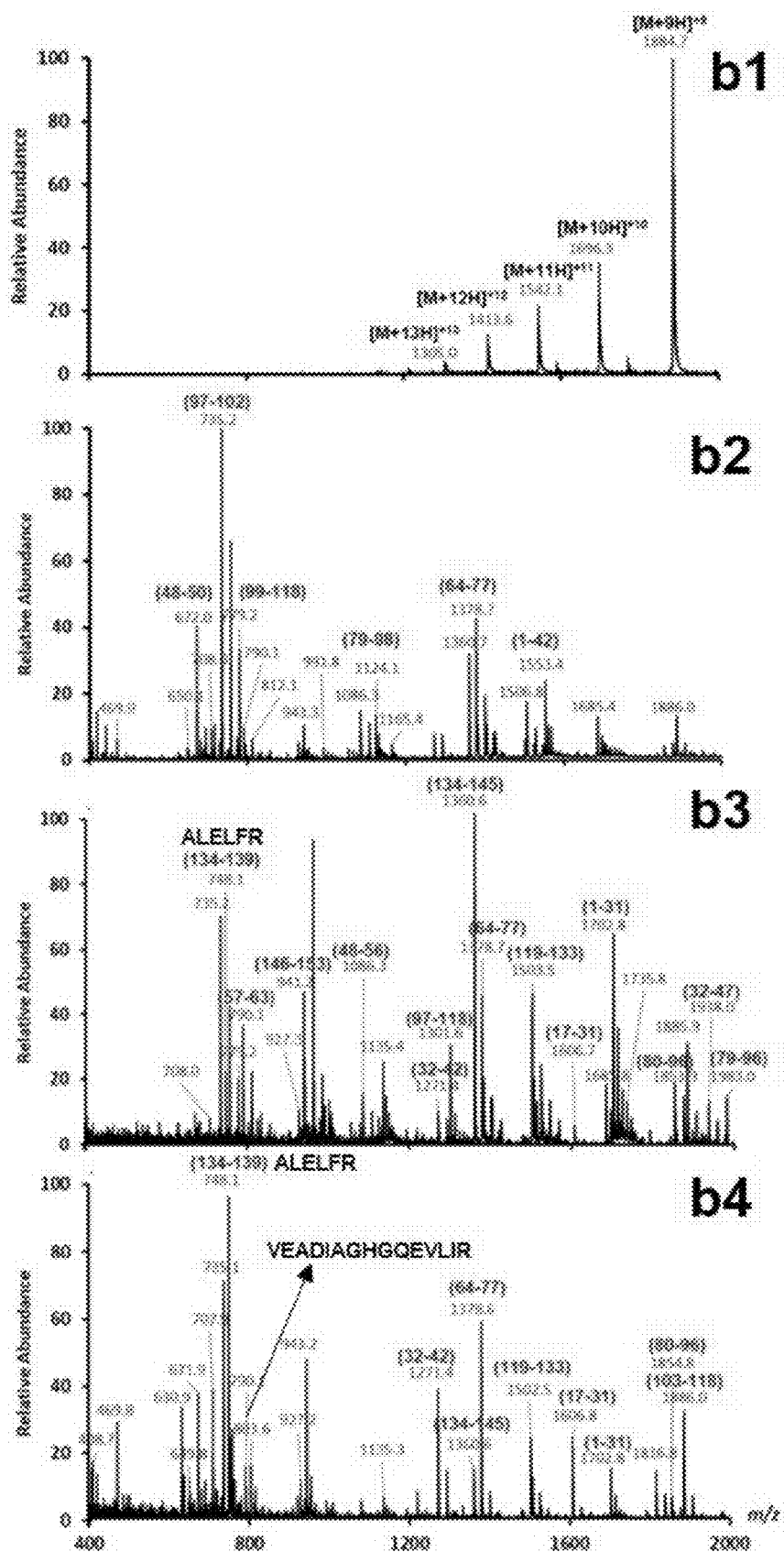
FIG. 21 shows mass spectra of multiple enzyme digestion of apomyoglobin with spectra of the digestion products after 10-min conventional digestion at room temperature (b1) and 10-min microwave-assisted digestion at 20 W net power within the microstrip resonator with endoproteinase Lys-c (b2), trypsin (b3) and a combination of Trypsin/Lys-C (b4)

In reviewing FIGS. 20 and 21, the spectra obtained after 10-min using a conventional digestion at room temperature can be compared to digestions from a 10-min microwave-assisted digestion at 20 W net power within the microstrip resonator system 200 using reactor 212. While only peaks associated with the intact protein were observed after 10-minutes conventional digestion at room temperature for the protein digestions (spectra a1, b1), a considerable number of peptide were observed after 10-minutes digestions using the microstrip rector 212 at 20 W net applied power (spectra a2-a4 and b2-b4).

Sequence coverages of 100%, 87% and 100% were achieved after 10-minutes digestion within the microstrip resonator for the Lys-C, trypsin and Trypsin/Lys-C digestion of cytochrome c, respectively (FIG. 20, spectra a2-a4). It should be further noted that sequence coverages obtained after 10-minutes using microwave reactor 212 were highly comparable to those obtained with the 20-hour conventional counterpart approach (95%, 95% and 92%, respectively) for the same protein (data not shown). It should be further noted that a greater number of missed cleavage peptides were observed using microwave reactor 212 as compared to the conventional counterpart. Also, the heme-containing peptide residue, 14-22, was not observed in digestion of cytochrome c with endoproteinase trypsin after 10-min microwave irradiation within microstrip reactor 212. However, a missed cleavage of the heme-containing peptide was observed when digesting cytochrome c with Trypsin/Lys-C during the same period of time. Only peptide residue 24-28 which is contained within the secondary structure motif of cytochrome c (alpha-helix to beta-strand) was not observed in either of the protocols. Peptide residue 29-39 (TGPNLHGLFGR) was not observed when using Lys-C endoproteinase which is an indication that the enzymes conserved their selectivity towards specific amino acids within microwave reactor 212.

For the enzymatic digestion of apomyoglobin, sequence coverages of 100%, 98% and 97% were achieved after 10-minutes digestion within the microstrip resonator system 200 using reactor 212 for the Lys-C, trypsin and Trypsin/Lys-C digestions of the protein, respectively (see FIG. 21, spectra b2-b4). Sequence coverages calculated when using the microwave approach were slightly higher than the ones obtained with the 20-hour conventional counterpart approach (95%, 90% and 92%, respectively) for the same protein. The peptide residue 57-63 was observed in the microwave-assisted protocol, but not in the conventional approach. Peptide sequence 57-63 arise from external helical regions within the protein structure. As in the case of cytochrome c (FIG. 20), a greater number of missed cleavage peptides were observed when using microwave assisted proteolysis. Peptide residues 17-31 (VEADIAGHGQEVLIR) and 134-139 (ALELFR) were not observed when using Lys-C endoproteinase which is another indication that the enzymes conserved their selectivity within the microwave-assisted protocol.

Figure 28:
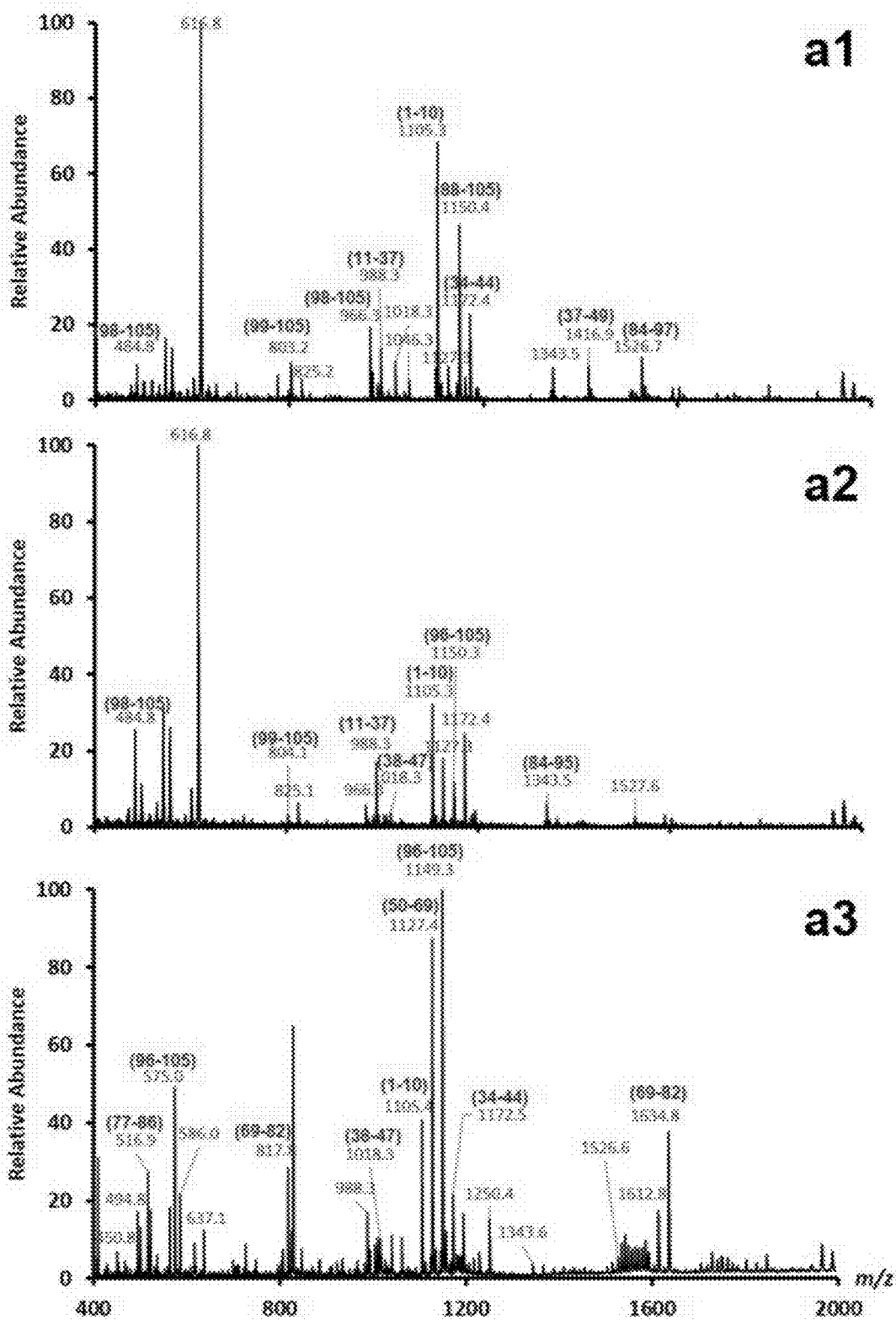
FIG. 28 shows mass spectra of a pepsin digestion of cytochrome c with spectra of the digestion products after 40-min conventional digestion at room temperature (a1), 40-min microwave-assisted digestion at 20 W net power within the microstrip resonator (a2), and 20-h conventional digestion at room temperature (a3)
Figure 29:
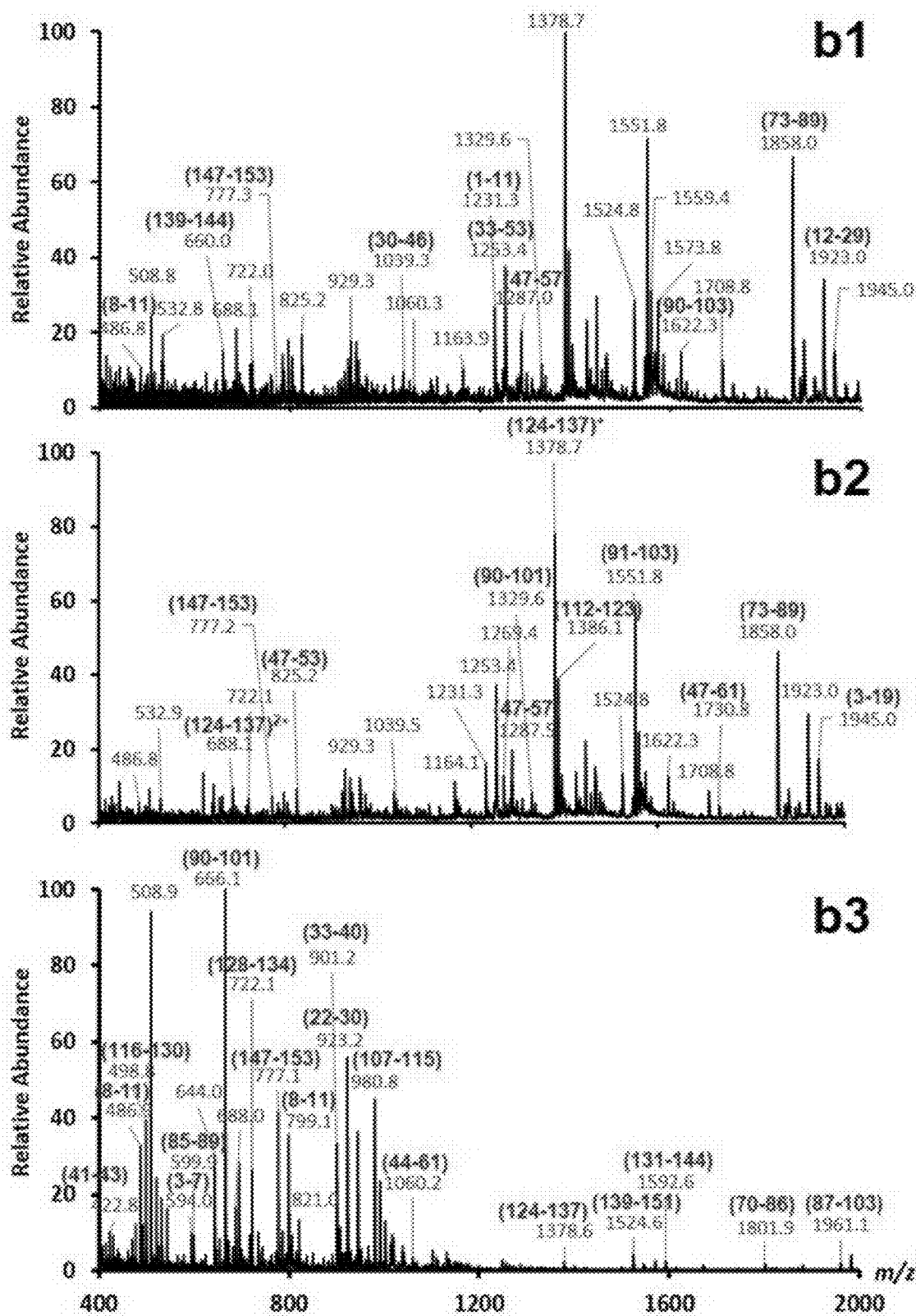
FIG. 29 shows mass spectra of a pepsin digestion of apomyoglobin with spectra of the digestion products after 40-min conventional digestion at room temperature (b1), 40-min microwave-assisted digestion at 20 W net power within the microstrip resonator (b2), and 20-h conventional digestion at room temperature (b3)

Microwave assisted digestion using pepsin of cytochrome c and apomyoglobin is shown in FIGS. 28 and 29, respectively. Pepsin cleaves proteins preferentially at the C-terminal side of phenylalanine, tryptophan, and tyrosine. Conventional and microwave-assisted digestions over a 40-min period are compared and yielded the same protein coverage of 85% for cytochrome c (see FIG. 28, spectra a1-a2). Only one additional missed cleavage residue, 37-49, was observed in the microwave-assisted protocol (spectrum a1) and not in the conventional approach (spectrum a2). Complete cytochrome c elucidation was obtained after the 20-hour conventional digestion (see FIG. 28, spectrum a3). A similar behavior was observed for the pepsin digestion of apomyoglobin and the spectra obtained after 40-min digestion with microwave acceleration (FIG. 29, spectrum b2) and using the conventional approach (FIG. 29, spectrum b1), and show the same peptide distribution. The spectrum obtained for the 20-hour conventional digestion protocol (FIG. 29, spectrum b3) exhibited smaller peptide fragments compared to the short incubation times using either 40 min protocol.

Modulated Microwave Dielectric Heating

In a further aspect of the present invention, the microwave dielectric heating of reactor 212 can be rapidly modulated, and thus the reaction temperature and kinetics of chemical or biochemical reactions can be carefully controlled within reactor 212. This capability permits active feedback with real-time monitoring of the reaction progress when coupled with mass spectrometer 120. Microwave power can be decreased or increased based upon the type of peptide (or reactants) observed within the mass spectra. This also permits reaction conditions to be changed based on changes to the local solvent composition (i.e. changes in overall heating based on changes in dielectric loss or ionic strength). Microwave power modulation also permits modulation of the types of ions observed in the mass spectrometer, allowing molecular intact ions to be observed under low power (or "OFF" conditions), and fragments of particular type to be observed as microwave power is increased.

Figure 30:
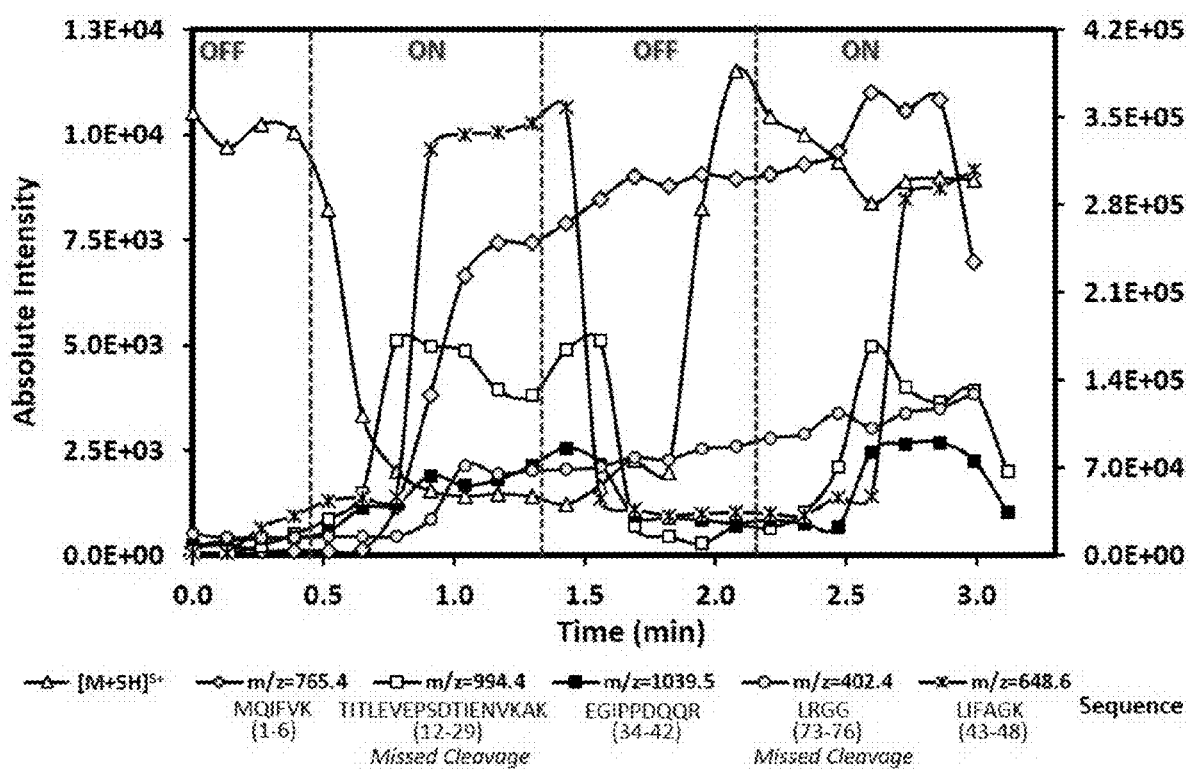
FIG. 30 shows a plot of peptide fragments resulting from microwave power modulation ("ON"-"OFF") during a trypsin digestion of ubiquitin.

Modulating microwave dielectric heating represents a significant advantage over the conventional convection or conduction heating approaches (i.e. resistive-element heating). Where convective heating relies on heat transfer from an external source, microwave dielectric heating can induce energy absorption by the solvent, reactants, or reactor itself. As shown in FIG. 30, an assessment of controlled digestion through microwave field modulation was explored by using the trypsin digestion of ubiquitin. The relative abundance of the intact protein and several characteristic peptides are plotted as a function of time and microwave irradiation. Microwave power of 40 W net applied power was modulated between "on" and "off" states for alternating periods of 30-seconds while allowing the reaction mixture to continuously electrospray from the nanospray emitter tip (distal end 212a) by application of +1.6 kV to the solution. Response of some peptide abundance to the microwave field is delayed due to the time required for the material to move from the heating region of reactor 212 to the nano-ESI emitter tip 212a. The intensity of the peaks associated with the intact protein, represented by the 5+ charge state in FIG. 30, was found to decrease substantially in response to the application of the microwave field, as might be expected. In opposition, the abundance of several peptides closely followed the microwave field. For example, internal peptide sequences 43-48 and 34-42 and those from missed cleavage (12-29 and 73-76) increased substantially in response to application of the microwave field and followed the microwave power modulation closely. It should be noted that the terminal peptide sequences MQIFVK and LRGG increased in abundance on the initial application of the microwave field, and then continued to increase even as the microwave heating ceased. These small terminal peptides are easily cleaved from the protein and may thus be less reliant on kinetic acceleration.

Modifying the Size of Reaction Region

Figure 31:
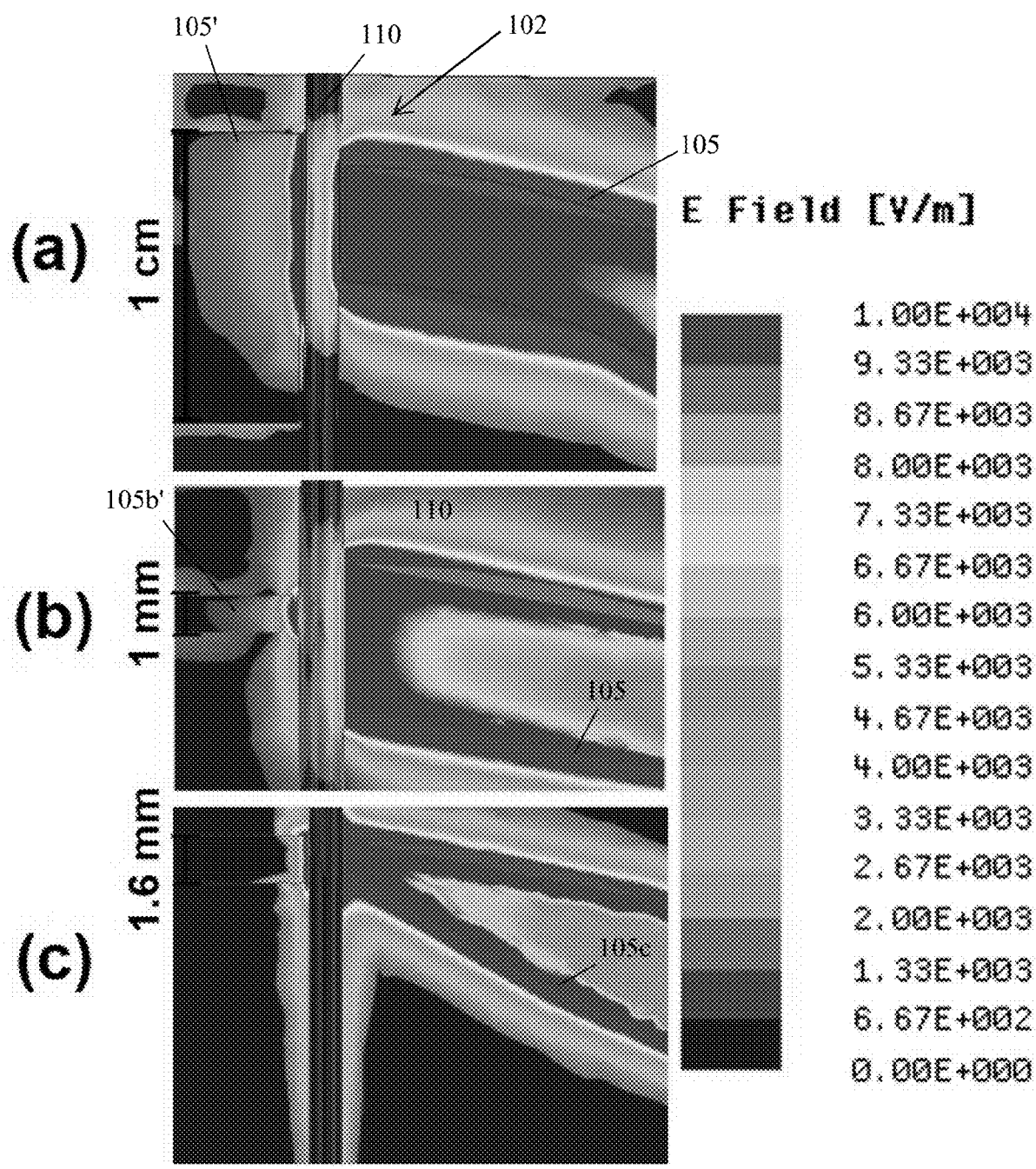
FIG. 31 shows simulations of the electromagnetic field distribution of microstrip systems with various antenna dimensions.

With reference to FIG. 31, the dimension and shape of the microstrip antenna within the capacitive gap 110 of the resonator 102 can be constricted or expanded depending on the desired reaction volume. Small contained volumes have lower heat capacity and are more amenable to heating modulation at a more rapid rate. Larger heating volumes have the opposite effect, but offer greater averaging of power and a lower gradient of thermal change. As shown in FIG. 31, the microwave antenna region can be modified to change the electric field strength in the capacitive gap 110. In the top image (a), the half-wave antenna 105 and counter ground antenna 105' (power OUT antenna) are of the same width. In the center image (b), the counter antenna 105b' has been reduced in width, to permit one half of the field intensity to be diminished. In the bottom image (c), the half-wave resonator antenna 105c has been shaped to permit heating in a much smaller area. Many variations of these dimensions can be applied as required by the heating application. It should also be noted that the capillary inner diameter can be changed to control the amount of sample volume being heated in this gap. Moreover, various microwave absorber or reflective materials can be incorporated or packed as described previously so as to control the rate of energy absorption when placed directly into the field.

Arrays of Heating Regions/Multi-Channel Heating

Figure 32:
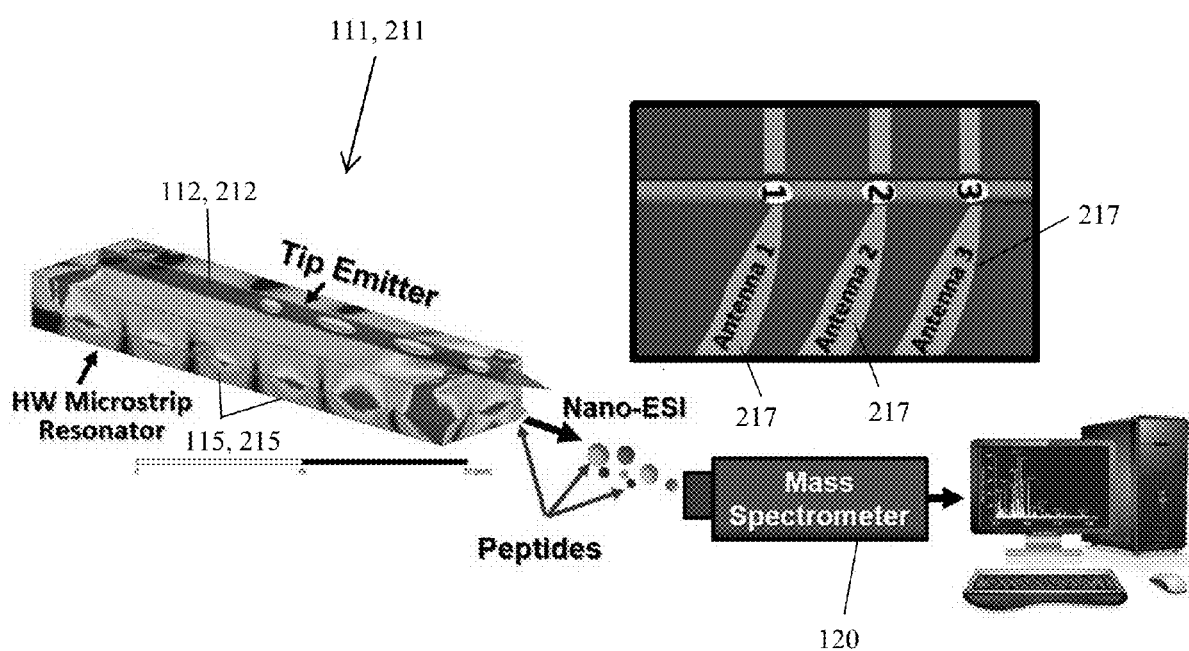
FIG. 32 is a schematic view of an exemplary microwave-assisted system setup with an array of heating regions within an internal groove along the resonator, with the figure insert illustrating the different heating regions (1-3) created by multiple antennas.

Turning now to FIG. 32, in another aspect of the present invention, microwave dielectric heating may permit selective control of heating power and area, and can be extended to a number of individual heating volumes placed in sequence, in an array, or in a multi-channel system 111, 211. As shown in FIG. 32, multiple capacitive gaps/heating volumes 115, 215 can be created for a single microreactor 112, 212. Microreactor can be in a flow-through system (e.g., reactor 212), or for a single sample (e.g., reactor 112). In this arrangement, each heating volume corresponds to a different chemical/biochemical reaction. As shown in FIG. 32, each volume 115, 215 can be heated independently by application of the microwave power to that particular antenna 217. Each region corresponds to a different chemical/biochemical modification in a manner similar to that described for multi-enzyme systems. For example, and without limitation thereto, one region 215a may contain trypsin and be placed next to a region 215b containing pepsin. Such an arrangement would permit observation of peptides resulting from each enzyme in isolation, or together, reflecting where microwave heating power was applied. It should be further noted that the array 111, 211 may be extended to an indeterminate number of regions, and may also be modulated as described here.

What is claimed is:

1. A microwave microstrip resonator apparatus comprising:
   a) a housing;
   b) a resonator within the housing;
   c) an output conductor within the housing and spaced apart from the resonator so as to define a capacitive gap therebetween;
   d) a reaction vessel configured to reside within the capacitive gap;
   e) a power supply coupled to the resonator whereby contents within the reaction vessel are heated when energy is supplied to the resonator by the power supply; and
   f) a microstrip antenna wherein the dimension and shape of the microstrip antenna is modified to change the electric field strength in the capacitive gap.

2. The microwave microstrip resonator apparatus of claim 1 further comprising:
   g) a mass spectrometer operably coupled to an outlet end of the reaction vessel wherein the contents within the reaction vessel are delivered to the mass spectrometer for analysis.

3. The microwave microstrip resonator apparatus of claim 2 further comprising:
   h) a second power supply coupled to the reaction vessel wherein electrospray ionization of the contents occurs when energy is supplied to the reaction vessel by the second power supply.

4. The microwave microstrip resonator apparatus of claim 3 wherein the electrospray ionization is nano-electrospray ionization.

5. The microwave microstrip resonator apparatus of claim 1 wherein the reaction vessel includes at least one immobilized enzyme therein.

6. The microwave microstrip resonator apparatus of claim 5 wherein the at least one immobilized enzyme is covalently bonded to an inner surface of the reaction vessel.

7. The microwave microstrip resonator apparatus of claim 5 wherein the at least one immobilized enzyme is attached to a bead and wherein the reaction vessel includes a packed bed of the beads.

8. The microwave microstrip resonator apparatus of claim 7 wherein the bead comprises a microwave absorbing material.

9. The microwave microstrip resonator apparatus of claim 2 further comprising:
   h) continuous flow system coupled to an inlet end of said reaction vessel.

10. The microwave microstrip resonator apparatus of claim 9 wherein the continuous flow system comprises one or more of liquid chromatography, flow injection analysis, capillary electrophoresis and multidimensional separations.

11. The microwave microstrip resonator apparatus of claim 1 wherein microwave dielectric heating of the reaction vessel is rapidly modulated to control reaction temperature and kinetics within the reaction vessel.

12. The microwave microstrip resonator apparatus of claim 1 comprising a plurality of microstrip antennae configured to vary the electric field strength in the capacitive gap along a length of the reaction vessel.

13. A method of online digestion and mass analysis comprising:
   a) providing a microwave microstrip resonator apparatus including:
      i) a housing;
      ii) a resonator within the housing;
      iii) an output conductor within the housing and spaced apart from the resonator so as to define a capacitive gap therebetween;
      iv) a reaction vessel including a sample wherein the reaction vessel is configured to reside within the capacitive gap;
      v) a power supply coupled to the resonator;

vi) a microstrip antenna wherein the dimension and shape of the microstrip antenna is modified to change the electric field strength in the capacitive gap; and
vii) a mass spectrometer operably coupled to an outlet end of the reaction vessel;

b) supplying a voltage to the resonator using the power supply to heat the sample within the reaction vessel to produce one or more digestion products; and c) performing mass spectrometry on the digestion products.

14. The method of claim 13 wherein the microwave microstrip resonator apparatus further includes a second power supply coupled to the reaction vessel wherein electrospray ionization of the contents occurs when a voltage is supplied to the reaction vessel by the second power supply.

15. A microwave microstrip resonator apparatus comprising:

a) a housing;
b) a resonator within the housing;
c) an output conductor within the housing and spaced apart from the resonator so as to define a capacitive gap therebetween, wherein the capacitive gap is configured to receive a reaction vessel therein;
d) a power supply coupled to the resonator and configured to heat contents within the reaction vessel when an electric field is supplied to the resonator by the power supply; and
e) a microstrip antenna, wherein the dimension and shape of the microstrip antenna is modified to change the strength of the electric field in the capacitive gap.

16. The microwave microstrip resonator apparatus of claim 15 comprising a plurality of microstrip antennae configured to vary the electric field strength in the capacitive gap along a length of the reaction vessel.

17. The microwave microstrip resonator apparatus of claim 15 further comprising:

f) a mass spectrometer configured to be operably coupled to an outlet end of the reaction vessel wherein the contents within the reaction vessel are delivered to the mass spectrometer for analysis.

18. The microwave microstrip resonator apparatus of claim 17 further comprising:

g) a second power supply configured to be coupled to the reaction vessel wherein electrospray ionization of the contents occurs when energy is supplied to the reaction vessel by the second power supply.

19. The microwave microstrip resonator apparatus of claim 18 further comprising:

h) a continuous flow system configured to be coupled to an inlet end of the reaction vessel, wherein the continuous flow system comprises one or more of liquid chromatography, flow injection analysis, capillary electrophoresis and multidimensional separations.

20. The microwave microstrip resonator apparatus of claim 15 wherein microwave dielectric heating of the reaction vessel is rapidly modulated to control reaction temperature and kinetics within the reaction vessel.

* * * * *